United States Patent
Pont et al.

(10) Patent No.: US 10,925,499 B2
(45) Date of Patent: Feb. 23, 2021

(54) SYSTEM AND METHOD FOR USING INTEGRATED SENSOR ARRAYS TO MEASURE AND ANALYZE MULTIPLE BIOSIGNATURES IN REAL TIME

(71) Applicant: SP Global, Inc., Chantilly, VA (US)

(72) Inventors: Dalton Pont, Sterling, VA (US); Dan B. Tolley, Purcellville, VA (US); Roger A. Mann, Herndon, VA (US); Joseph Tolley, Purcellville, VA (US); John V. Chiochetti, Annapolis, MD (US)

(73) Assignee: SP GLOBAL, INC., Chantilly, VA (US)

( * ) Notice: Subject to any disclaimer, the term of this patent is extended or adjusted under 35 U.S.C. 154(b) by 176 days.

(21) Appl. No.: 15/909,141

(22) Filed: Mar. 1, 2018

(65) Prior Publication Data

US 2018/0249919 A1    Sep. 6, 2018

Related U.S. Application Data

(60) Provisional application No. 62/466,022, filed on Mar. 2, 2017.

(51) Int. Cl.
*A61B 5/02* (2006.01)
*A61B 5/024* (2006.01)
(Continued)

(52) U.S. Cl.
CPC .......... *A61B 5/02427* (2013.01); *A61B 5/002* (2013.01); *A61B 5/0006* (2013.01);
(Continued)

(58) Field of Classification Search
USPC .................................................. 600/300–301
See application file for complete search history.

(56) References Cited

U.S. PATENT DOCUMENTS

| 8,204,786 B2 | 6/2012 | LeBoeuf et al. |
| 8,251,903 B2 | 8/2012 | LeBoeuf et al. |

(Continued)

FOREIGN PATENT DOCUMENTS

| WO | 1987000286 A1 | 1/1987 |
| WO | 2010045247 A1 | 4/2010 |

(Continued)

OTHER PUBLICATIONS

Heikenfeld, J. C., Advanced Sweat Sensor Adhesion, Hermetic, and Fluidic Strategies, U.S. Appl. No. 62/023,233, Provisional Patent Application filed Jul. 11, 2014; Entire Document.

(Continued)

*Primary Examiner* — Nicole F Lavert
(74) *Attorney, Agent, or Firm* — Neo IP

(57) ABSTRACT

Systems and methods including a device having integrated sensor arrays constructed and configured to measure and analyze multiple biosignatures concurrently in real time and a mobile application to control the device, process data, and transmit data wirelessly via at least one network to at least one remote computing device for analyzing the multiple biosignatures and cross-correlation with at least one external factor resulting in the creation of personal and situation profiles for continued on-going real time monitoring, refinement, alerting, and action recommendations.

20 Claims, 35 Drawing Sheets

(51) Int. Cl.
- A61B 5/0205 (2006.01)
- A61B 5/1455 (2006.01)
- A61B 5/11 (2006.01)
- A61B 5/00 (2006.01)
- A61B 5/0402 (2006.01)
- A61B 10/00 (2006.01)
- A61B 5/145 (2006.01)
- G16H 10/40 (2018.01)

(52) U.S. Cl.
CPC ........ *A61B 5/0022* (2013.01); *A61B 5/02055* (2013.01); *A61B 5/02438* (2013.01); *A61B 5/04023* (2013.01); *A61B 5/1113* (2013.01); *A61B 5/14517* (2013.01); *A61B 5/14532* (2013.01); *A61B 5/14542* (2013.01); *A61B 5/14546* (2013.01); *A61B 5/14552* (2013.01); *A61B 10/0064* (2013.01); *G16H 10/40* (2018.01); *A61B 5/0017* (2013.01); *A61B 2503/10* (2013.01)

(56) References Cited

U.S. PATENT DOCUMENTS

| | | | |
|---|---|---|---|
| 8,788,002 | B2 | 7/2014 | LeBoeuf et al. |
| 8,961,415 | B2 | 2/2015 | LeBoeuf et al. |
| 9,427,191 | B2 | 8/2016 | LeBoeuf |
| 9,579,024 | B2 | 2/2017 | Nyberg et al. |
| 9,622,725 | B2 | 4/2017 | Pizer et al. |
| 9,636,061 | B2 | 5/2017 | Nyberg et al. |
| 9,645,133 | B2 | 5/2017 | Pizer et al. |
| 9,883,827 | B2 | 2/2018 | Nyberg et al. |
| 2007/0100666 | A1* | 5/2007 | Stivoric ............ G16H 40/63 705/3 |
| 2008/0249584 | A1* | 10/2008 | Scheurer ............ A61N 1/0553 607/14 |
| 2015/0126834 | A1 | 5/2015 | Wang et al. |
| 2015/0173677 | A1 | 6/2015 | Chetelat et al. |
| 2015/0184097 | A1 | 7/2015 | Landschof |
| 2015/0217449 | A1* | 8/2015 | Meier ............ G06N 3/008 700/257 |
| 2015/0297104 | A1 | 10/2015 | Chen et al. |
| 2016/0256066 | A1 | 9/2016 | Chetelat et al. |
| 2016/0262667 | A1 | 9/2016 | Pizer et al. |
| 2016/0287148 | A1 | 10/2016 | Pizer et al. |
| 2016/0290952 | A1 | 10/2016 | Pizer et al. |
| 2017/0223844 | A1 | 8/2017 | Pizer et al. |

FOREIGN PATENT DOCUMENTS

| | | |
|---|---|---|
| WO | 2013152087 A3 | 1/2014 |
| WO | 2014197822 A3 | 4/2015 |
| WO | 2015058055 A1 | 4/2015 |
| WO | 2015058064 A1 | 4/2015 |
| WO | 2015184072 A1 | 12/2015 |
| WO | 2015184084 A3 | 1/2016 |
| WO | 2015184097 A3 | 1/2016 |
| WO | 2016007944 A2 | 1/2016 |
| WO | 2016049019 A1 | 3/2016 |
| WO | 2016061362 A3 | 6/2016 |
| WO | 2016130905 A1 | 8/2016 |
| WO | 2016134235 A1 | 8/2016 |
| WO | 2016138087 A1 | 9/2016 |
| WO | 2016144529 A1 | 9/2016 |
| WO | 2017058806 A1 | 9/2016 |

OTHER PUBLICATIONS

Ackerman, S., U.S. Appl. No. 62/130,030, Provisional Patent Application; Entire Document.

Ackerman, S., U.S. Appl. No. 62/130,039, Provisional Patent Application; Entire Document.

Ackerman, S., U.S. Appl. No. 62/130,047, Provisional Patent Application; Entire Document.

Doytchinova MD, A. et. al., Subcutaneous Nerve Activity and Spontaneous Ventricular Arrhythmias in Ambulatory Dogs, Heart Rhythm. Mar. 2015 ; 12(3): 612-620. doi:10.1016/j.hrthm2014.11.007.

Gao, et al.,"Fully integrated wearable sensor arrays for multiplexed in situ perspiration analysis",Nature, vol. 529, No. 7587, pp. 509-514 (Jan. 2016).

Godek, "Sweat Rates and Fluid Turnover in Professional Football Players: A Comparison of National Football League Linemenand Backs," Journal of Athletic Training 2008;43(2):184-189.

Hagen, J. A., Sweat Simulation, Collection, and Sensing Systems, U.S. Appl. No. 61/620,069, Provisional Patent Application filed Apr. 4, 2012; Entire Document.

Heikenfeld, J. "Let Them See You Sweat", IEEE Spectrum, Nov. 2014, p. 46.

Heikenfeld, J. C., Advanced Adhesives for Chronological Sweat Sensors, U.S. Appl. No. 62/074,295, Provisional Patent Application filed Nov. 3, 2014; Entire Document.

Heikenfeld, J. C., Device Construction for Prolonged and Reliable Sweat Stimulation and Sensing, U.S. Appl. No. 62/003,707, Provisional Patent Application filed May 28, 2014; Entire Document.

Heikenfeld, J. C., Sweat Stimulation for Integrated or Repeated Biosensing, U.S. Appl. No. 61/892,859, Provisional Patent Application filed Oct. 18, 2013; Entire Document.

Heikenfeld, J. C., Sweat Sensor With Chronological Assurance, U.S. Appl. No. 62/003,675, Provisional Patent Application filed May 28, 2014; Entire Document.

Jiang, Z. et. al. , Using Skin Sympathetic Nerve Activity to Estimate Stellate Ganglion Nerve Activity in Dogs, Heart Rhythm, http://dx.doi.org/10.1016/j.hrthm.2015.02.012.

Liu, et al."Implementation of a microfluidic conductivity sensor—A potential sweat electrolyte sensing system for dehydration detection," in Conf Proc IEEE Eng Med Biol Soc, 2014:1678-81, 5 pgs.

Nyberg, S.A., U.S. Appl. No. 15/839,957, Non-Provisional Patent Application; Entire Document.

Parkel, T. et al., "A Human Centred Design Approach for System Integration of Wearables" p. 90, CSEM SA, Scientific and Technical Report 2015.

Robinson, E. A., et. al. , Estimating sympathetic tone by recording subcutaneous nerve activity in ambulatory dogs, J Cardiovasc Electrophysiol. Jan. 2015 ; 26(1): 70-78. doi:10.1111/jce.12508.

Rose, D. P. et. al., "Adhesive RFID Sensor Patch for Monitoring of Sweat Electrolytes", IEEE Transactions on Biomedical Engineering, Paper ID # TBME-00773-2014-R1, Manuscript received Jun. 18, 2014; revised Sep. 10, 2014; accepted Nov. 6, 2014, DOI10.1109/TBME.2014.2369991.

Sawka et al., "Exercise and Fluid Replacement," American College of Sports Medicine (AGSM) (1996) Position Stand Med SciSports Exerc 28: i-vii.

Schwartz, I. L. & Thaysen, J. H., "Excretion of Sodium and Potassium in Human Sweat", The Rockefeller nstitute for Medical Research, New York, NY, published Sep. 28, 1955, pp. 114-120.

Sonner, Z. et. al, The microfluidics of the eccrine sweat gland, including biomarker partitioning, transport, and biosensing implications, Biomicrofluidics 9, 031301, published May 15, 2015, entire document.

Taylor, N. A.S., & Machado-Moreira, C. A., "Regional variations in transepidermal water loss, eccrine sweat gland density, sweat secretion rates and electrolyte composition in resting and exercising humans", Extreme Physiology & Medicine 2013, 2:4 http://www.extremephysiolmed.com/content/2/1/4.

Tolley, D. B., U.S. Appl. No. 62/466,022, Provisional Patent Application; Entire Document.

* cited by examiner

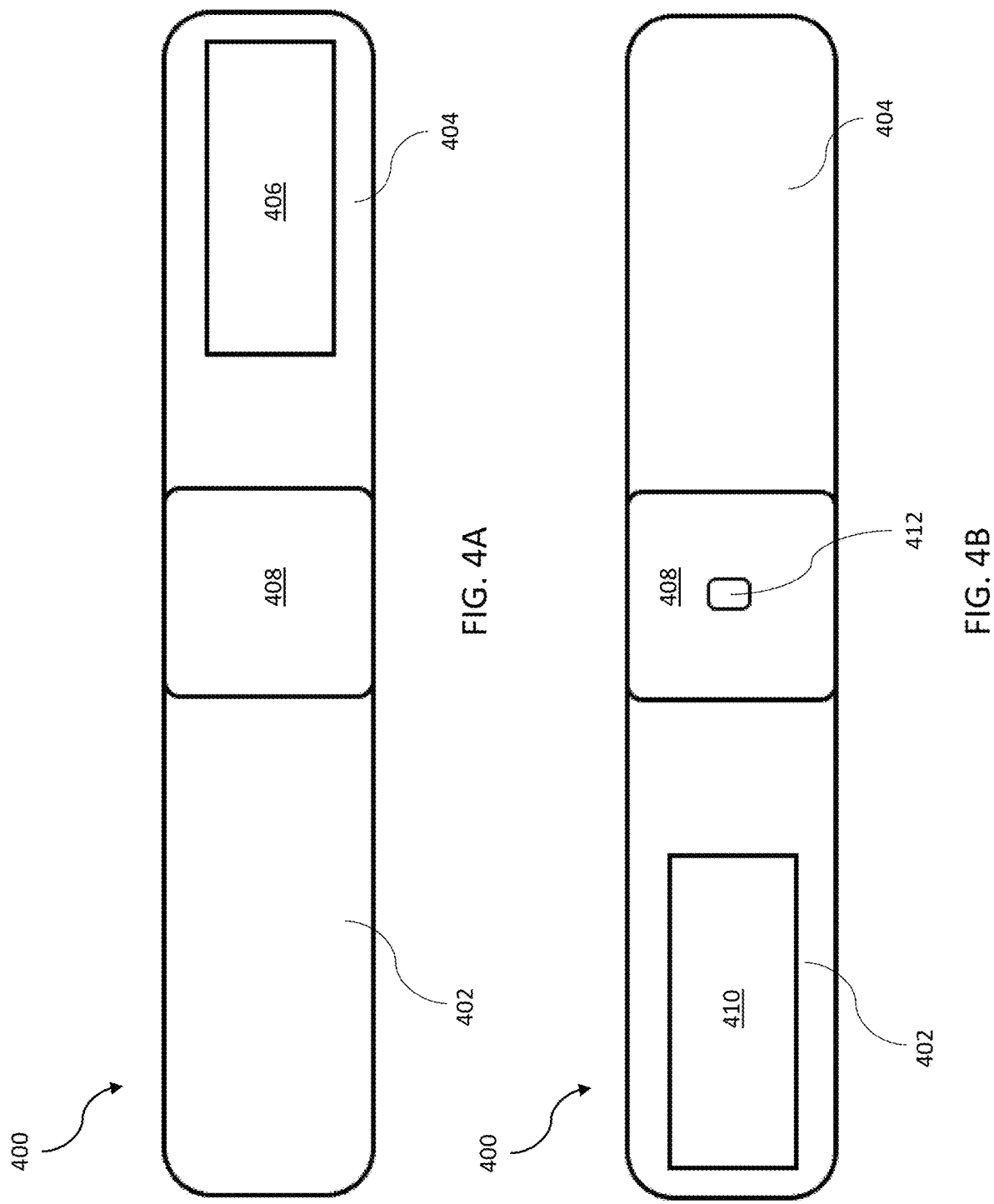

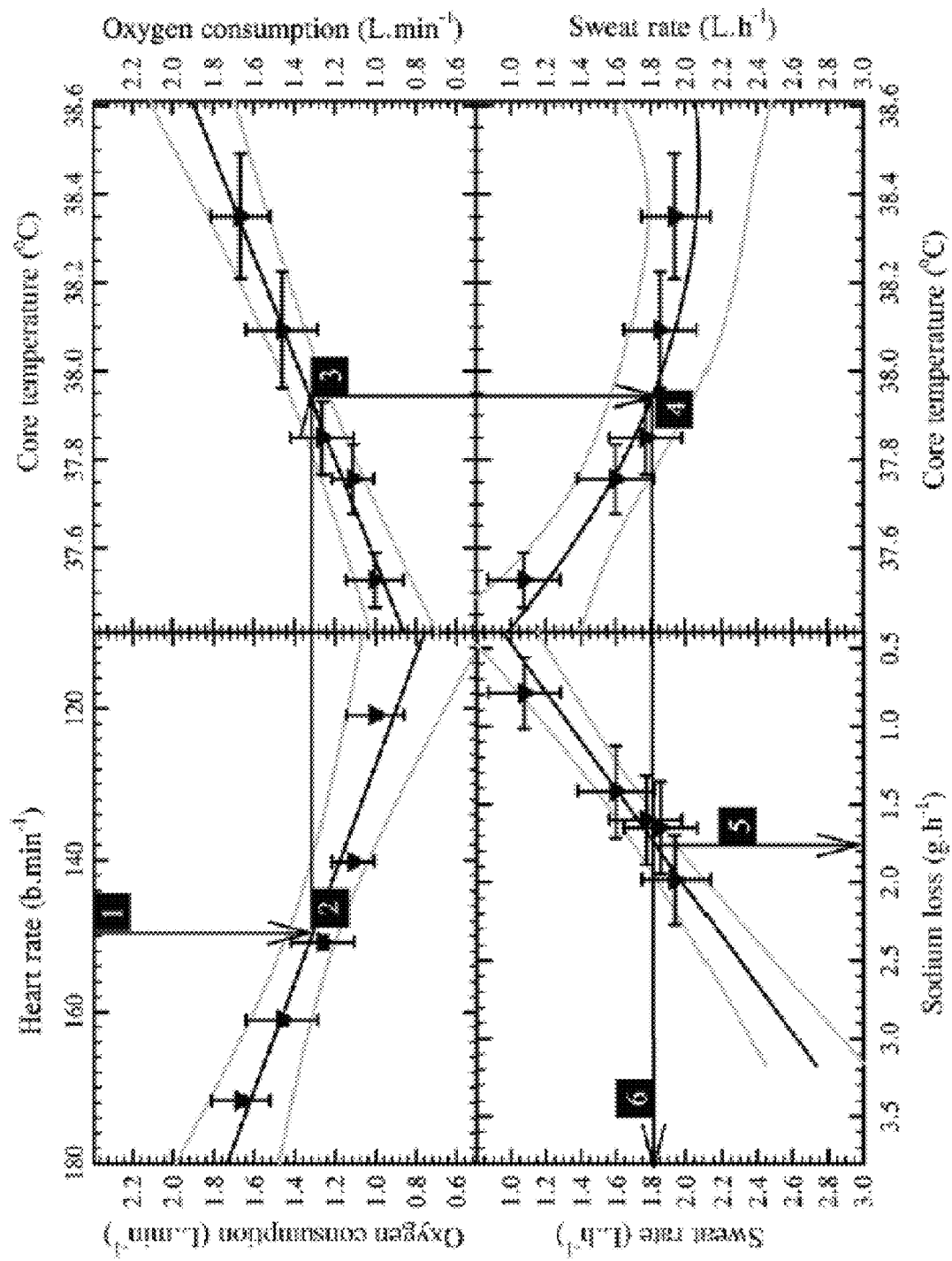
PRIOR ART FIG. 7A

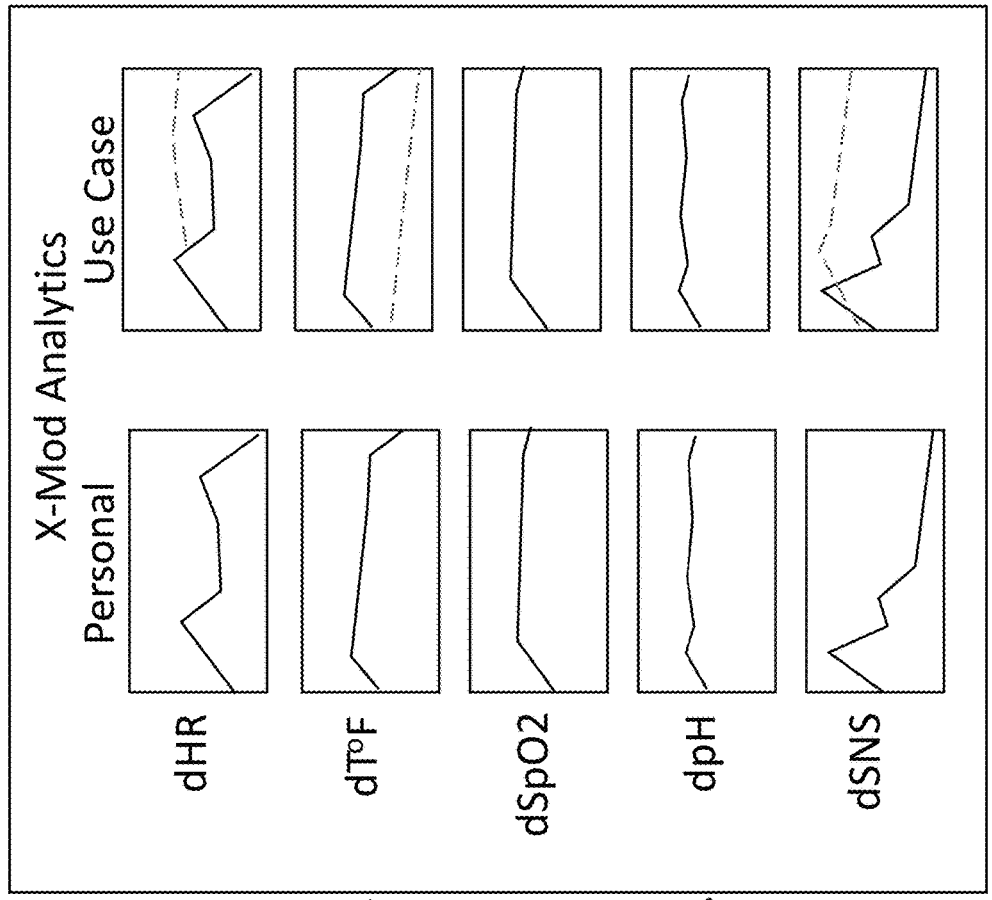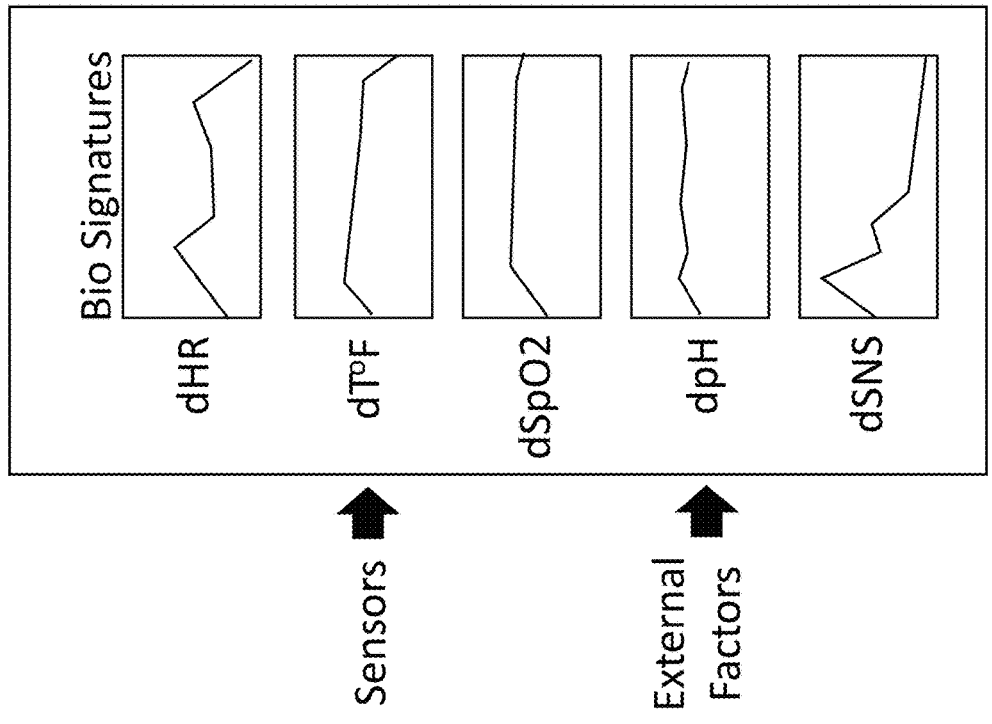
FIG. 8A

Early Warning System Monitoring Abnormal Bio-Activity

| Sensor | BioSignature | Symbol | Percent Change per Minute | | | Validated by External |
|---|---|---|---|---|---|---|
| | | | Caution Level Change Threshold | Alert Level Change Threshold | Critical Level Change Threshold | |
| LED/Photon | Heart Rate | dHR | 25 | 50 | 75 | Clinical Count |
| LED/Photon | Blood Ox | dBOx | 2 | 4 | 6 | Blood Gas |
| LED/Photon | Blood Pressure | dBp | 5 | 10 | 20 | Blood Pressure Aneroid |
| SNS | Cardio Stress | dCs | 10 | 20 | 30 | ECG |
| SNS | Pulm Blood Ox Stress | dBOs | 10 | 20 | 30 | ECG |
| SNS | Physical Stress | dPs | 10 | 20 | 30 | ECG |
| SNS | Gastro Stress | dCs | 10 | 20 | 30 | ECG |
| SNS | ThermoReg Stress | dTRs | 10 | 20 | 30 | ECG |
| SNS | Glucose Stress | dGs | 10 | 20 | 30 | ECG |
| SNS | Arterial Stress | dAts | 10 | 20 | 30 | ECG |
| SNS | Acid Stress | dAcs | 5 | 10 | 15 | Litmus Test |
| Ion reactive | pH | dpH | 5 | 10 | 15 | Litmus Test |
| ISE | Sodium | dNa | 20 | 35 | 50 | Scale and Ion Spectrograph |
| ISE | Potassium | dK | 20 | 35 | 50 | Ion Spectrograph |
| Thermister | Skin Temp | dTsk | 5 | 10 | 15 | Thermometer |
| Infrared | Core Temp | dTc | 5 | 10 | 15 | Thermometer |
| Thermister | Ambient Temp | dTa | 25 | 50 | 75 | Thermometer |
| Spectroscopy | Glucose | dGs | 5 | 10 | 15 | Finger Prick One Touch |
| Accelerometer | Impact | dI | 10 | 25 | 50 | Clinical Observation |
| Accelerometer | Shiver | dSh | 10 | 25 | 50 | Clinical Observation |
| Accelerometer | Seizure | dSe | 10 | 25 | 50 | Clinical Observation |
| Stab Antibodies | Antigen +/- | dAn | n/A | True State | n/a | WHO Approved RDT with Blood Draws to Lab |

| Parameters | Malaria |
|---|---|
| Heart Rate (HR) | Increased HR due to RBC lysis, leading to decreased oxygen delivery to peripheral tissues. The HR will increase as a compensatory mechanism to try to delivery more oxygen to end organs. It will also be elevated due to the inflammatory response from Plasmodium infection. |
| Blood Oxygen (SpO2) | Remains fairly normal until late stages of malarial disease, despite RBC destruction. Pulmonary edema occurs in late stages. |
| Blood Pressure | Remains fairly normal until middle to late stages of malarial disease. Patient in the 'hot' stage of malaria tend to vasodilate, have decreased fluid intake, and vomit. These effects contribute to lower systemic resistance. As the cardiac output increases to compensate (increased HR), there will be a point where it cannot maintain a normal blood pressure. At this point, the blood pressure will start to fall. Towards the end stage, profound cardiovascular collapse and vasoplegia occur, and BP continues to fall. |
| SNS | Increased Gastro Stress |
| Stab Antibodies | Positive presence of target antigen = color is blue |
| Ambient Temperature (Ta) |  |
| Skin Temperature (Tsk) | After prodromal symptoms occur, which usually last several days, a classic sign of malarial infection is elevated skin temperature. They are described as intermittent, synchronous with erythrocyte schizont rupture at 48-72 hour intervals. |
| Sodium Loss (Na) | Higher sodium loss in sweating, however, this may be balanced with high sodium loss in patient with vomiting |
| Potassium Loss (K) | Higher potassium loss in sweating, however, may be balanced with increased renal excretion as a balance mechanism when sodium is lost in emesis. |
| Glucose | Plasmodium cannot perform aerobic metabolism. They utilize host glucose ineffectively, increase glucose consumption and produce lactic acid. Those infected will be hypoglycemic. |
| pH | Relatively normal until mid to late stages when end organs become oxygens starved causing anaerobic metabolism and increased $CO_2$ production. Blood pH will begin to fall once serum bicarbonate can no longer buffer appropriately. |
| Accelerometer | The classic malarial paroxysm is broken down into three stages: cold, hot, and sweat. Initially the patient starts feeling cold, even in warm climates. They become apprehensive. Then they start shaking violently due to rigors. In children, the core temperature starts to rise, and can lead to febrile seizures and convulsions. Convulsions also seen the 'cerebral malaria', where a person develops ischemic encephalopathy due to microcapillary blockage from swollen RBCs. This also leads to seizure activity. |
| Clinical Observation | Increased fatigue due to worsening anemia (from RBC lysis) will lead to decreased activity, less food consumption, and less interaction with others |
| Social Media Analytics | Decreased activity |

FIG. 11B

| Parameters | Myocardial Infarction |
|---|---|
| Heart Rate (HR) | HR generally will increase during a heart attack due to pain, decreased cardiac output leading to compensatory increase in HR, and generation of arrhythmias depending on where the coronary occlusion has occurred. Occasionally, HR can decrease under specific conditions such as SA node ischemia and the Bezold-Jarisch syndrome. |
| Blood Oxygen (SpO2) | Generally remains normal. Situation where it decreases if there is a massive MI leading to poor cardiac output and acute heart failure. |
| Blood Pressure | BP can increase or decrease. An acute MI can cause sympathetic stimulation leading to increased HR and thus BP. More often, BP is slightly lower than normal since cardiac output is usually lower than normal after a heart attack. |
| SNS | Increased Cardio Stress |
| Stab Antibodies | |
| Ambient Temperature (Ta) | |
| Skin Temperature (Tsk) | Will generally remain normal or decrease slightly. In cases where skin temperature of distal extremities is noticeably decreased, it could be an indicator of cardiogenic shock and is an ominous sign. |
| Sodium Loss (Na) | Low sodium has been demonstrated during an acute myocardial infarction. The level remains low on day 1, and returns to normal by day 4. Improvement in serum sodium indicates better clinical outcomes. Studies assume this is due to increased permeability of the sarcolemma. |
| Potassium Loss (K) | Low potassium has been demonstrated during an acute myocardial infarction. The level usually returns to normal by day 3. Hypokalemia might be due to increased circulating catecholamines during and after AMI. |
| Glucose | Patients having AMI are generally hyperglycemic in the first 24 hours. This is due to increased sympathetic stimulation increasing glycogenolysis, decreased sensitivity to insulin at the endothelial level, and the possibility of preexisting diabetes either diagnosed or undiagnosed. |
| pH | Can be normal or abnormal depending on if the heart can maintain distal perfusion. |
| Accelerometer | No significant diagnostic information |
| Clinical Observation | Will complain of chest pain that radiates to the jaw, between the shoulder blades/back, and/or down the left arm. Sometimes patients will complain of chest pressure or a burning sensation. |
| Social Media Analytics | Refugee may report a feeling of unwellness over several days |

FIG. 11C

| Parameters | Alcohol Poisoning |
|---|---|
| Heart Rate (HR) | Generally, you will see an increase in HR during the intoxication phase where BAC is increasing as alcohol itself is a vasodilator. Dehydration from increased diuresis and vomiting will increase HR. Some people will develop cardiac arrhythmias such as SVT due to the toxic effect of alcohol on the SA and AV nodes. In severe cases when BAC ~ 0.5%, the heart rate slows dramatically. |
| Blood Oxygen (SpO2) | Alcohol is a direct poison to the mitochondria and aerobic metabolism. This causes 'histiotoxic hypoxia', where blood oxygen and partial pressures are normal, but the tissue can't use it because the cells have become 'non-functional'. |
| Blood Pressure | Because alcohol is a vasodilator, it generally leads to a mild decrease in blood pressure, even as HR attempts to compensate. Also, these people tend to be volume depleted due to diarrhea and vomiting, thus lowering the BP. |
| SNS | Increased Gastro Stress. Arterial Stress |
| Stab Antibodies | |
| Ambient Temperature (Ta) | |
| Skin Temperature (Tsk) | Large doses of alcohol will decrease core body temperature, and increase peripheral vasodilation. At first you will see an increase in skin temperature, but this is fleeting. During the course of intoxication, skin temperature will decrease to below normal levels for a prolonged period of time. |
| Sodium Loss (Na) | Can be either normal or low (hyponatremia). With increased diuresis due to the effects of alcohol on antidiuretic hormone, sodium is lost in the urine. Also, with increased frequency of vomiting and diarrhea, sodium is lost with whole water. |
| Potassium Loss (K) | Most studies show potassium is low (hypokalemia) in the acute intoxication phase, both from vomiting |
| Glucose | Alcohol tends to increase insulin secretion from the pancreas in the acute phase leading to transient hypoglycemia. |
| pH | Any form of alcohol ingestion leads to an acidic state due to acidification of the blood, increase binding to bicarbonate buffer, and loss of bicarbonate with increased diuresis. pH will be low in moderate to severely intoxicated people. |
| Accelerometer | If intoxication has caused a severe decrease in blood glucose levels, seizure activity may occur. High oscillatory rhythmic changes in accelerometer variables will be noted. |
| Clinical Observation | Decrease in location check-in as habitual use of alcohol will lead to decreased functional activity, decreased socialization. |
| Social Media Analytics | Alcohol itself in chronic abuse situations leads to dizziness, headaches, lack of ability to concentrate, depression, and anxiety. |

FIG. 11D

| Parameters | Drug Use/Overdose |
|---|---|
| Heart Rate (HR) | Drug dependent. Opioids/heroin will cause bradycardia in high doses. Sympathomimetics such as PCP, meth, cocaine will increase HR until the drug has been metabolized. Time course is usually hours. |
| Blood Oxygen (SpO2) | Opioid like drugs will lead to respiratory depression and decrease blood oxygenation. |
| Blood Pressure | Variable depending on co-morbid conditions with drug use (such as hydration status, energy status, cardiac function, etc.) Sympathomimetics will generally increase BP (especially cocaine) for several hours. Half-life of cocaine with normal liver and renal function is 60 minutes. |
| SNS | Increased Gastro Stress. Arterial Stress |
| Stab Antibodies | |
| Ambient Temperature (Ta) | |
| Skin Temperature (Tsk) | Variable |
| Sodium Loss (Na) | Variable |
| Potassium Loss (K) | Variable |
| Glucose | Variable |
| pH | Variable |
| Accelerometer | Variable depending on drug intake. Will drugs that cause limbic dissociation such as PCP or a sympathomimetic such as methamphetamine, refugees may exhibit increased motor movement due to hallucinations or rage. |
| Clinical Observation | Decreased check in due to drug use/addiction. Poor activities of daily living. If they do check in, they may appear disheveled, show signs of intoxication such as rage, inability to sustain a conversation, poorly coordinated motor function. |
| Social Media Analytics | Variable |

FIG. 11E

| Parameters | Diarrheal Diseases |
|---|---|
| Heart Rate (HR) | Increase over 1-2 days due to decrease in effective circulating volume (ECF) |
| Blood Oxygen (SpO2) | Will remain normal |
| Blood Pressure | Decreased due to lower ECF |
| SNS | Increased All Stress |
| Stab Antibodies | Presence of Target Antigen, color = Blue |
| Ambient Temperature (Ta) | |
| Skin Temperature (Tsk) | Decreased over several days as body will increase vasoconstriction, decrease sweat production, in an attempt to maintain homeostasis. |
| Sodium Loss (Na) | Increased |
| Potassium Loss (K) | Increased |
| Glucose | |
| pH | |
| Accelerometer | No significant diagnostic information early in disease state. Likely lethargy and decreased movement if refugee is not treated. |
| Clinical Observation | Decreased due to lethargy. Will complain of loose stools and poor PO intake. May complain of fever or blood in stools if associated with organism. |
| Social Media Analytics | Refugee dependent. |

FIG. 11F

| Parameters | Fight |
|---|---|
| Heart Rate (HR) | Fight or flight syndrome will increase HR |
| Blood Oxygen (SpO2) | Normal or slight increase |
| Blood Pressure | Will increase due to fight or flight. |
| SNS | Increased Gastro Stress |
| Stab Antibodies | |
| Ambient Temperature (Ta) | |
| Skin Temperature (Tsk) | Will likely increase due to increase metabolic rate, thus increasing sweat. |
| Sodium Loss (Na) | Normal |
| Potassium Loss (K) | Normal |
| Glucose | WNL or may increase slightly due to fight or flight (catabolism and glycogenolysis), but effect will be delayed. |
| pH | Norm |
| Accelerometer | Will show significant vector changes during fight. |
| Clinical Observation | Observe for signs of combat, such as hematomas in likely areas (e.g., arms, face, eyes, mouth). Observe for broken ribs (ground combat). |
| Social Media Analytics | Refugee dependent. |

FIG. 11G

| Parameters | Measles |
|---|---|
| Heart Rate (HR) | Disease generally seen in non-immunized children. Baseline HR may be elevated, could be increased if patient dehydrated from diarrhea and emesis. |
| Blood Oxygen (SpO2) | No noticeable changes |
| Blood Pressure | Could be decreased in those who are dehydrated due to diarrhea and emesis. |
| SNS | Increased Gastro Stress |
| Stab Antibodies | Presence of Target Antigen, color = Blue |
| Ambient Temperature (Ta) | |
| Skin Temperature (Tsk) | First sign of measles is usually a high fever (often > 104 degrees F) that typically lasts 4-7 days. |
| Sodium Loss (Na) | Decreased with severe diarrhea and emesis, otherwise would be normal |
| Potassium Loss (K) | Decreased with severe diarrhea and emesis, otherwise would be normal |
| Glucose | No noticeable changes |
| pH | May be alkalotic if patient has severe diarrhea and emesis, otherwise would be normal |
| Accelerometer | No significant diagnostic information |
| Clinical Observation | Prodromal phase lasts 7-14 days before fever begins. Patients have malaise and anorexia associated with decreased activity. |
| Social Media Analytics | May complain of typical rash seen with viral disease, however, mostly a viral illness that affects children. |

FIG. 11H

| Parameters | Acute Respiratory Infections (Flu) |
|---|---|
| Heart Rate (HR) | Will either be normal or increased due to inflammatory response from illness, potential hypoxia due to infected lung |
| Blood Oxygen (SpO2) | Can be normal or decreased depending on severity of disease |
| Blood Pressure | Will likely be normal unless infection is causing systemic inflammatory response thus decreasing blood pressure |
| SNS | Increased Pulmonary Stress |
| Stab Antibodies | Presence of Target Antigen, color = Blue |
| Ambient Temperature (Ta) | |
| Skin Temperature (Tsk) | Can be lower, normal or elevated depending on degree and stage of infection. |
| Sodium Loss (Na) | No noticeable changes |
| Potassium Loss (K) | No noticeable changes |
| Glucose | Either normal or elevated depending on degree and stage of infection. |
| pH | Either normal or decreased depending on degree and stage of infection. |
| Accelerometer | No significant diagnostic information |
| Clinical Observation | Decreased depending on degree and stage of infection. At check in, refugee may appear normal (early stage) or appear very sick with signs such as increased sweating, tachypnea (increased respiratory rate), short of breath with minimal exertion, febrile, and complain of a productive cough that may or may not be associated with blood. |
| Social Media Analytics | Refugee dependent. |

FIG. 11I

| Parameters | Malnutrition |
|---|---|
| Heart Rate (HR) | Will likely see increased HR during the initial phase, then a decrease in HR as energy stores begin to deplete |
| Blood Oxygen (SpO2) | In advanced states of protein loss, a refugee may have poor breathing/ventilatory function (loss of intercostal and diaphragmatic muscle mass). This will lead to hypoxia and hypercarbia. |
| Blood Pressure | Few studies have shown that malnourished children tend to have increased BP compared to control groups. Alternatively, in extreme condition, poor heart function (poor vitamin intake, specifically Vitamin B1 aka. Thiamine which is a co-enzyme needed for proper cardiac muscle and nerve function) due to decreased stroke volume and bradycardia will cause low BP. Also, poor albumin/protein intake will lower effective circulating volume, also contributing to lower BP. |
| SNS | Increase in Gastro Stress |
| Stab Antibodies | |
| Ambient Temperature (Ta) | |
| Skin Temperature (Tsk) | Will decrease over time as immune function and metabolism are negatively affected due to decreased protein/vitamin intake. The ability to maintain a normal body temperature will worsen. |
| Sodium Loss (Na) | Serum sodium concentration is generally decreased due to overabundance of free water compared to sodium level (even though they have sodium overload). Will also decrease due to diarrhea. |
| Potassium Loss (K) | Total body potassium is decreased in all malnourished due to decreased intake and poor muscle mass. Most serum levels are subclinical however in overt malnourished cases or concomitant diarrhea the serum level will be low. |
| Glucose | In general, the mean fasting blood glucose level in malnourished children is lower compared to controls, however, the difference may not be noticeable in the early stages of protein energy malnutrition. |
| pH | Depends on the ability of the kidneys to maintain bicarbonate buffer. However, as cardiac output decreases, renal function will worsen and retention of free water will increase. This will dilute plasma electrolytes which may lead to decreased pH. Also, hypercarbia from poor ventilatory function will increase blood serum acidity. |
| Accelerometer | No significant diagnostic information |
| Clinical Observation | Refugee will appear gaunt, reveal loss of muscle mass, and may appear jaundiced. Loss of energy or activity are common symptoms. Decreased GI use will lead to gut wasting and bacterial translocation, thus leading to sepsis. Note: The prevalence of malnutrition in hospitals around the world is up to 50%. |
| Social Media Analytics | Refugee dependent. |

SYSTEM AND METHOD FOR USING INTEGRATED SENSOR ARRAYS TO MEASURE AND ANALYZE MULTIPLE BIOSIGNATURES IN REAL TIME

BACKGROUND OF THE INVENTION

1. Field of the Invention

The present invention relates to biometric signal detection and analytics of data collected from multiple sensors and external sources.

2. Description of the Prior Art

It is generally known in the prior art to provide sensors to detect biometric data and to provide biosignatures.

WIPO Publication No. WO2016061362 for sweat sensing device communication security and compliance by inventors Heikenfeld, et al., filed Oct. 15, 2015 and published Jun. 16, 2016, is directed to an invention that addresses confounding difficulties involving continuous sweat analyte measurement. Specifically, the invention provides: at least one component capable of monitoring whether a sweat sensing device is in sufficient contact with a wearer's skin to allow proper device operation; at least one component capable of monitoring whether the device is operating on a wearer's skin; at least one means of determining whether the device wearer is a target individual within a probability range; at least one component capable of generating and communicating alert messages to the device user(s) related to: wearer safety, wearer physiological condition, compliance with a requirement to wear a device, device operation; compliance with a behavior requirement, or other purposes that may be derived from sweat sensor data; and the ability to utilize aggregated sweat sensor data that may be correlated with information external to the device to enhance the predictive capabilities of the device.

Published article by Rose, et al., in IEEE Transactions on Biomedical Engineering, Nov. 6, 2014, pages 1-9, discusses an adhesive RFID sensor patch for monitoring of sweat electrolytes.

U.S. Publication No. 20160287148 for device for measuring biological fluids by inventors Pizer, et al., filed Jun. 9, 2016 and published Oct. 6, 2016, is directed to a flexible, multi-layered device for automatically sensing sweat biomarkers, storing and transmitting sensed data via wireless network to a computing device having software applications operable thereon for receiving and analyzing the sensed data. The device is functional in extreme conditions, including extremely hot temperatures, extremely cold temperatures, high salinity, high altitude, extreme pHs, and/or extreme pressures.

U.S. Pat. No. 9,579,024 for system and method for measuring biological fluid biomarkers by inventors Nyberg, et al., filed Jun. 9, 2016 and issued Feb. 28, 2017, is directed to systems and methods of analyzing biological fluid biomarkers, calculating biomarker data, transmitting data to a transceiver device, and storing the data and/or analytics in a database and/or on at least one remote computer server.

U.S. Pat. No. 9,622,725 for method for manufacturing a biological fluid sensor by inventors Pizer, et al., filed Jun. 9, 2016 and issued Apr. 18, 2017, is directed to a method of fabrication for a physiological sensor with electronic, electrochemical and chemical components. The fabrication method comprises steps for manufacturing an apparatus comprising at least one electrochemical sensor, a microcontroller, and a transceiver. The physiological sensor is operable to analyze biological fluids such as sweat.

U.S. Pat. No. 9,820,692 for wearable electrochemical sensors by inventors Wang, et al., filed May 10, 2013 and issued Nov. 21, 2017, is directed to methods, structures, devices and systems for fabricating and implementing electrochemical biosensors and chemical sensors. In one aspect, a method of producing an epidermal biosensor includes forming an electrode pattern onto a coated surface of a paper-based substrate to form an electrochemical sensor, the electrode pattern including an electrically conductive material and an electrically insulative material configured in a particular design layout, and attaching an adhesive sheet on a surface of the electrochemical sensor having the electrode pattern, the adhesive sheet capable of adhering to skin or a wearable item, in which the electrochemical sensor, when attached to the skin or the wearable item, is operable to detect chemical analytes within an external environment.

U.S. Pat. No. 10,448,852 for system and method for non-invasive autonomic nerve activity monitoring by inventors Chen, et al., filed Dec. 9, 2013 and issued Oct. 22, 2019, is directed to a system and method for monitoring nerve activity in a subject. The system includes a plurality of electrodes placed in proximity to skin of the subject, an amplifier electrically connected to the electrodes and configured to generate a plurality of amplified signals corresponding to electrical signals received from the subject through the electrodes, and a signal processor. The signal processor applies a high-pass filter to the amplified signals to generate filtered signals from the amplified signals, identifies autonomic nerve activity in the plurality of filtered signals; and generates an output signal corresponding to the filtered signals. The high-pass filter attenuates a plurality of the amplified signals having frequencies that correspond to heart muscle activity during a heartbeat.

WIPO Publication No. WO2017058806 for wearable sensor arrays for in-situ body fluid analysis by inventors Javey, et al., filed Sep. 27, 2016 and published Apr. 6, 2017, is directed to a wearable sensing platform including sensors and circuits to sense aspects of a user's state by analyzing bodily fluids, such as sweat and/or urine, and a user's temperature. A sensor array senses a plurality of different body fluid analytes, optionally at the same time. A signal conditioner is coupled to the sensor array. The signal conditioner conditions sensor signals. An interface is configured to transmit information corresponding to the conditioned sensor signals to a remote computing device. The wearable sensing platform may include a flexible printed circuit board to enable the wearable sensing platform, or a portion thereof, to conform to a portion of the user's body.

Published article by Gao, et al. entitled "Fully integrated wearable sensor arrays for multiplexed in situ perspiration analysis" in Nature, vol. 529, no. 7587, pages 509-514 (January 2016), discusses a flexible integrated sensing array for simultaneous and selective screening of a panel of biomarkers in sweat.

U.S. Pat. No. 8,204,786 for physiological and environmental monitoring systems and methods by inventors LeBoeuf, et al., filed Jan. 6, 2011 and issued Jun. 19, 2012, is directed to systems and methods for monitoring various physiological and environmental factors, as well as systems and methods for using this information for a plurality of useful purposes. Real-time, noninvasive health and environmental monitors include a plurality of compact sensors integrated within small, low-profile devices. Physiological and environmental data is collected and wirelessly transmitted into a wireless network, where the data is stored and/or processed. This information is then used to support a variety of useful methods, such as clinical trials, marketing studies, biofeedback, entertainment, and others.

U.S. Pat. No. 8,251,903 for noninvasive physiological analysis using excitation-sensor modules and related devices and methods by inventors LeBoeuf, et al., filed Oct. 23, 2008 and issued Aug. 28, 2012, is directed to methods and apparatus for qualifying and quantifying excitation-dependent physiological information extracted from wearable sensors in the midst of interference from unwanted sources. An organism is interrogated with at least one excitation energy, energy response signals from two or more distinct physiological regions are sensed, and these signals are processed to generate an extracted signal. The extracted signal is compared with a physiological model to qualify and/or quantify a physiological property. Additionally, important physiological information can be qualified and quantified by comparing the excitation wavelength-dependent response, measured via wearable sensors, with a physiological model.

U.S. Pat. No. 8,961,415 for methods and apparatus for assessing physiological conditions by inventors LeBoeuf, et al., filed Feb. 22, 2010 and issued Feb. 24, 2015, is directed to a monitoring apparatus and methods for assessing a physiological condition of a subject. At least two types of physiological information are detected from a subject via a portable monitoring device associated with the subject, and an assessment of a physiological condition of the subject is made using the at least two types of physiological information, wherein each type of physiological information is individually insufficient to make the physiological condition assessment. Environmental information from a vicinity of a subject also may be detected, and an assessment of a physiological condition of the subject may be made using the environmental information in combination with the physiological information. Exemplary physiological information may include subject heart rate, subject activity level, subject tympanic membrane temperature, and subject breathing rate. Exemplary environmental information may include humidity level information in the vicinity of the subject. An exemplary physiological condition assessment may be subject hydration level.

U.S. Pat. No. 8,788,002 for light-guiding devices and monitoring devices incorporating same by inventors LeBoeuf, et al., filed Dec. 14, 2012 and issued Jul. 22, 2014, is directed to a monitoring device configured to be attached to the ear of a person including a base, an earbud housing extending outwardly from the base that is configured to be positioned within an ear of a subject, and a cover surrounding the earbud housing. The base includes a speaker, an optical emitter, and an optical detector. The cover includes light transmissive material that is in optical communication with the optical emitter and the optical detector and serves as a light guide to deliver light from the optical emitter into the ear canal of the subject wearing the device at one or more predetermined locations and to collect light external to the earbud housing and deliver the collected light to the optical detector.

U.S. Pat. No. 9,427,191 for apparatus and methods for estimating time-state physiological parameters by inventor LeBoeuf, filed Jul. 12, 2012 and issued Aug. 30, 2016, is directed to a method of determining a value of a physiological parameter for a subject at a selected state includes obtaining, via a device attached to the subject, a value of the physiological parameter of the subject at a particular time-of-day, and applying a time-dependent relationship function to the obtained physiological parameter value via a processor to determine a value of the physiological parameter at the selected state.

U.S. Publication No. 20160256066 for method and system to measure physiological signals or to electrically stimulate a body part by inventors Chetelat, et al., filed Oct. 21, 2013 and published Sep. 8, 2016, is directed to a body electrode system including a set of standalone electrodes units for measuring physiological signals of a body part and/or electrically stimulate a body part. A connecting garment provides electrical connection between each standalone unit of the set. Each unit of the set is individually positionable at a specific chosen position onto the body to be sensed and/or stimulated. The garment is electrically connectable to said units, preferably after placement of said set onto the body.

U.S. Pat. No. 10,105,072 for measurement device for measuring bio-impedance and/or a bio-potential of a human or animal body by inventors Chetelat, et al., filed Dec. 19, 2014 and issued Oct. 23, 2018, is directed to a measurement device for measuring a bio-impedance and/or a bio-potential of a human or animal body and adapted to be worn on the body, including: at least two electrode sensors. Each of the at least two electrode sensors includes a first electrical contact configured to be in electrical contact with the skin of the body when the system is worn, and a second electrical contact. A single electrical connector electrically connects the at least two electrode sensors with each other via the second electrical contact. An active device is configured to cooperate with a subset of the at least two electrode sensors such that the potential of the electrical connector is substantially equal to a projected potential determined from the potential of the first electrical contact of each electrode sensor of the subset when the measurement device is worn.

SUMMARY OF THE INVENTION

The present invention relates to systems and methods including a device having integrated sensor arrays constructed and configured to measure and analyze multiple biosignatures concurrently in real time and a mobile application to control the device, process data, and transmit data wirelessly via at least one network to at least one remote computing device for analyzing the multiple biosignatures and cross-correlation with at least one external factor resulting in the creation of personal and situation profiles for continued on-going real time monitoring, refinement, alerting, and action recommendations.

In one embodiment, the present invention provides a system for using integrated sensor arrays to measure and analyze multiple biosignatures from a human or an animal including an apparatus for sensing and analyzing at least two biosignatures, wherein the apparatus includes a biosensor array, an electronic core, and at least one antenna, at least one remote transceiver device, and at least one remote computer server, wherein the biosensor array includes at least two sensors, wherein two or more of the at least two sensors are of differing modalities, wherein the electronic core includes a multiplexer, at least one analog-to-digital converter, and at least one processor, wherein the apparatus analyzes at least two biosignatures from the at least two sensors, calculates at least one output datum of the at least two biosignatures, and transmits the at least one output datum to the at least one remote transceiver device, wherein the at least one remote transceiver device transmits the at least one output datum to the at least one remote computer server or at least one remote computing device or database for storage, wherein the apparatus and the at least one remote transceiver device have real-time or near-real-time two-way communication, wherein the at least one remote transceiver device and the at least one remote computer server have real-time or near-real-time communication, and wherein the at least one remote computer server is operable to analyze apparatus data using cross-modal analytics.

In another embodiment, the present invention provides a system for using integrated sensor arrays to measure and analyze multiple biosignatures from a human or an animal including an apparatus for sensing and analyzing at least two biosignatures, wherein the apparatus includes a biosensor array, an electronic core, and at least one antenna, at least one remote transceiver device, and at least one remote computer server, wherein the biosensor array includes at least two sensors, wherein two or more of the at least two sensors are of differing modalities, wherein the electronic core includes a multiplexer, at least one analog-to-digital converter, and at least one processor, wherein the apparatus analyzes at least two biosignatures from the at least two sensors, calculates at least one output datum of the at least two biosignatures, and transmits the at least one output datum to the at least one remote transceiver device, wherein the at least one remote transceiver device transmits the at least one output datum to the at least one remote computer server or at least one remote computing device or database for storage, wherein the apparatus and the at least one remote transceiver device have real-time or near-real-time two-way communication, wherein the at least one remote transceiver device and the at least one remote computer server have real-time or near-real-time communication, wherein at least one external factor is stored on the at least one remote computer server, wherein the at least one remote computer server is operable to analyze apparatus data using cross-modal analytics, wherein the at least one remote computer server is operable to detect at least one biosignature change and at least one rate of change of the at least one biosignature change, wherein the at least one remote computer server is operable to generate at least one alert when the at least one biosignature change and the at least one rate of change of the at least one biosignature is greater than a designated threshold.

In yet another embodiment, the present invention includes a method for using integrated sensor arrays to measure and analyze multiple biosignatures from a human or an animal, the method including providing an apparatus for sensing and analyzing at least two biosignatures, wherein the apparatus includes at least two sensors, at least one analog-to-digital converter, a multiplexer, a processor, and at least one antenna, at least one remote transceiver device, and at least one remote computer server, wherein the at least one remote transceiver device and the apparatus are operable for two-way cross-communication in real time or near-real time, each of the at least two sensors sensing at least one biosignature of the human or the animal, the processor converting the at least one biosignature of the human or the animal into at least one output datum using at least one algorithm, one or more of the at least one antenna transmitting the at least one output datum to the at least one remote transceiver device via the two-way communication with the apparatus, the at least one remote transceiver device sharing or transmitting the at least one datum with the at least one remote computer server or at least one remote computing device or database for storage, and the at least one remote computer server analyzing apparatus data using cross-modal analytics.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 4A illustrates a top perspective view of one embodiment of the invention as a wrist band.

FIG. 4B illustrates a bottom perspective view of one embodiment of the invention as a wrist band.

FIG. 7A is a quadrant diagram for estimating fluid and sodium replacement rates.

FIG. 8A illustrates one embodiment of a system for cloud biosignature analytics.

FIG. 10 shows one embodiment of an assessment table of an early warning system monitoring abnormal bio-activity.

FIG. 11A shows a table of sensors that can be incorporated into the device and their associated biosignatures related to malaria.

FIG. 11B shows a table of sensors that can be incorporated into the device and their associated biosignatures related to myocardial infarction.

FIG. 11C shows a table of sensors that can be incorporated into the device and their associated biosignatures related to alcohol poisoning.

FIG. 11D shows a table of sensors that can be incorporated into the device and their associated biosignatures related to drug use and/or overdose.

FIG. 11E shows a table of sensors that can be incorporated into the device and their associated biosignatures related to diarrheal diseases.

FIG. 11F shows a table of sensors that can be incorporated into the device and their associated biosignatures related to a fight.

FIG. 11G shows a table of sensors that can be incorporated into the device and their associated biosignatures related to measles.

FIG. 11H shows a table of sensors that can be incorporated into the device and their associated biosignatures related to acute respiratory infections.

FIG. 11I shows a table of sensors that can be incorporated into the device and their associated biosignatures related to malnutrition.

DETAILED DESCRIPTION

Figure 1:
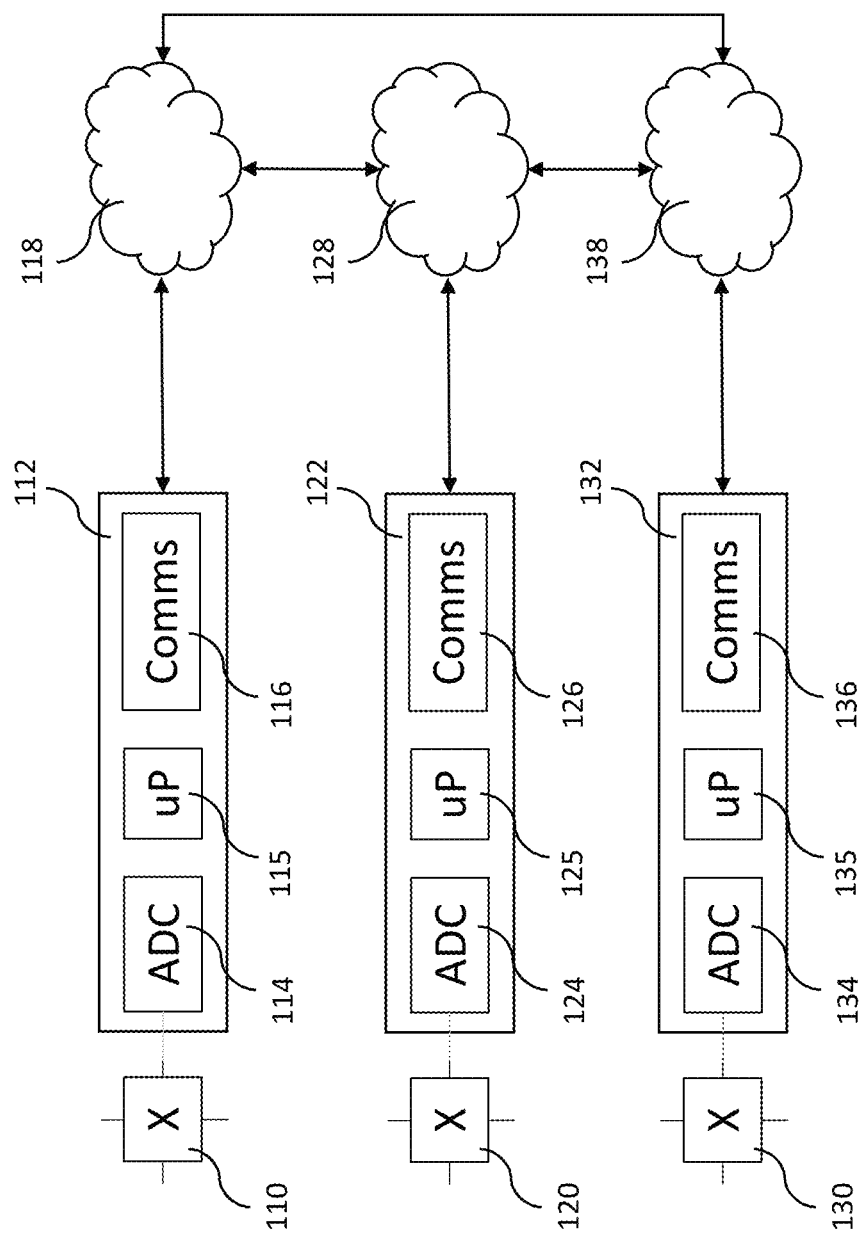
FIG. 1 illustrates a single modality sensor that evaluates one biosignature string.

The present invention is generally directed to systems and methods including a device having integrated sensor arrays constructed and configured to measure and analyze inputs from sensors that provide multiple biosignatures in real time. The system includes a mobile application to control, process, and transmit data. The systems and methods are operable to transmit the inputs and/or data wirelessly via at least one communications network to a remote computing device for analyzing the multiple biosignatures, calculating data related to the multiple biosignatures, and storing the data in a database, on the remote computing device, and/or a remote computer server or cloud-based computing system.

In one embodiment, the present invention provides a system for using integrated sensor arrays to measure and analyze multiple biosignatures from a human or an animal including an apparatus for sensing and analyzing at least two biosignatures, wherein the apparatus includes a biosensor array, an electronic core, and at least one antenna, at least one remote transceiver device, and at least one remote computer server, wherein the biosensor array includes at least two sensors, wherein two or more of the at least two sensors are of differing modalities, wherein the electronic core includes a multiplexer, at least one analog-to-digital converter, and at least one processor, wherein the apparatus analyzes at least two biosignatures from the at least two sensors, calculates at least one output datum of the at least two biosignatures, and transmits the at least one output datum to the at least one remote transceiver device, wherein the at least one remote transceiver device transmits the at least one output datum to the at least one remote computer server or at least one remote computing device or database for storage, wherein the apparatus and the at least one remote transceiver device have real-time or near-real-time two-way communication, wherein the at least one remote transceiver device and the at least one remote computer server have real-time or near-real-time communication, and wherein the at least one remote computer server is operable to analyze apparatus data using cross-modal analytics.

In another embodiment, the present invention provides a system for using integrated sensor arrays to measure and analyze multiple biosignatures from a human or an animal including an apparatus for sensing and analyzing at least two biosignatures, wherein the apparatus includes a biosensor array, an electronic core, and at least one antenna, at least one remote transceiver device, and at least one remote computer server, wherein the biosensor array includes at least two sensors, wherein two or more of the at least two sensors are of differing modalities, wherein the electronic core includes a multiplexer, at least one analog-to-digital converter, and at least one processor, wherein the apparatus analyzes at least two biosignatures from the at least two sensors, calculates at least one output datum of the at least two biosignatures, and transmits the at least one output datum to the at least one remote transceiver device, wherein the at least one remote transceiver device transmits the at least one output datum to the at least one remote computer server or at least one remote computing device or database for storage, wherein the apparatus and the at least one remote transceiver device have real-time or near-real-time two-way communication, wherein the at least one remote transceiver device and the at least one remote computer server have real-time or near-real-time communication, wherein at least one external factor is stored on the at least one remote computer server, wherein the at least one remote computer server is operable to analyze apparatus data using cross-modal analytics, wherein the at least one remote computer server is operable to detect at least one biosignature change and at least one rate of change of the at least one biosignature change, wherein the at least one remote computer server is operable to generate at least one alert when the at least one biosignature change and the at least one rate of change of the at least one biosignature is greater than a designated threshold.

In yet another embodiment, the present invention includes a method for using integrated sensor arrays to measure and analyze multiple biosignatures from a human or an animal, the method including providing an apparatus for sensing and analyzing at least two biosignatures, wherein the apparatus includes at least two sensors, at least one analog-to-digital converter, a multiplexer, a processor, and at least one antenna, at least one remote transceiver device, and at least one remote computer server, wherein the at least one remote transceiver device and the apparatus are operable for two-way cross-communication in real time or near-real time, each of the at least two sensors sensing at least one biosignature of the human or the animal, the processor converting the at least one biosignature of the human or the animal into at least one output datum using at least one algorithm, one or more of the at least one antenna transmitting the at least one output datum to the at least one remote transceiver device via the two-way communication with the apparatus, the at least one remote transceiver device sharing or transmitting the at least one datum with the at least one remote computer server or at least one remote computing device or database for storage, and the at least one remote computer server analyzing apparatus data using cross-modal analytics.

Referring now to the drawings in general, the illustrations are for the purpose of describing a preferred embodiment of the invention and are not intended to limit the invention thereto.

Prior art sensors, as shown in FIG. 1, use only one type of sensor (e.g., image/photon, spectroscopy, electrochemical, inertial, thermal, radiofrequency (RF)) on a single target (e.g., sweat, skin, air, sound) and each sensor has its own circuit to measure, process, store, and communicate data. In the example shown in FIG. 1, a first sensor 110 of a first modality type has a first circuit 112 that includes a first analog-to-digital converter (ADC) 114, a first microprocessor 115, and a first transceiver 116. Data is sent from the first transceiver 116 to a first cloud 118. A second sensor 120 of a second modality type has a second circuit 122 that includes a second analog-to-digital converter (ADC) 124, a second microprocessor 125, and a second transceiver 126. Data is sent from the second transceiver 126 to a second cloud 128. A third sensor 130 of a third modality type has a third circuit 132 that includes a third analog-to-digital converter (ADC) 134, a third microprocessor 135, and a third transceiver 136. Data is sent from the third transceiver 136 to a third cloud 138. Data sent to the first cloud 118 is operable to be sent to the second cloud 128 and/or the third cloud 138. Data sent to the second cloud 118 is operable to be sent to the first cloud 118 and/or the third cloud 138. Data sent to the third cloud 118 is operable to be sent to the first cloud 118 and/or the second cloud 128.

In other prior art cases, a circuit is designed to handle multiple sensors of a single type/modality (e.g., electrochemical sensors to analyze different analytes in sweat). In both prior art cases, the circuit is fine-tuned for a single modality and all signals are processed independently and analyzed independently. Data is stored, viewed, and/or displayed as separate biosensor data. None of the prior art includes multi-modal analytics. The prior art uses multiple devices to access the data using many independent applications for each single modality. This results in unconnected user functions and users are limited to results from a single modality.

Examples of prior art sensors include the following issued patents and/or publications for biological fluid sensors: U.S. Pat. Nos. 9,579,024, 9,622,725, 9,636,061, 9,645,133, and 9,883,827 and U.S. Publication Nos. 20160262667, 20160287148, and 20170223844, each of which is incorporated herein by reference in its entirety.

Figure 2:
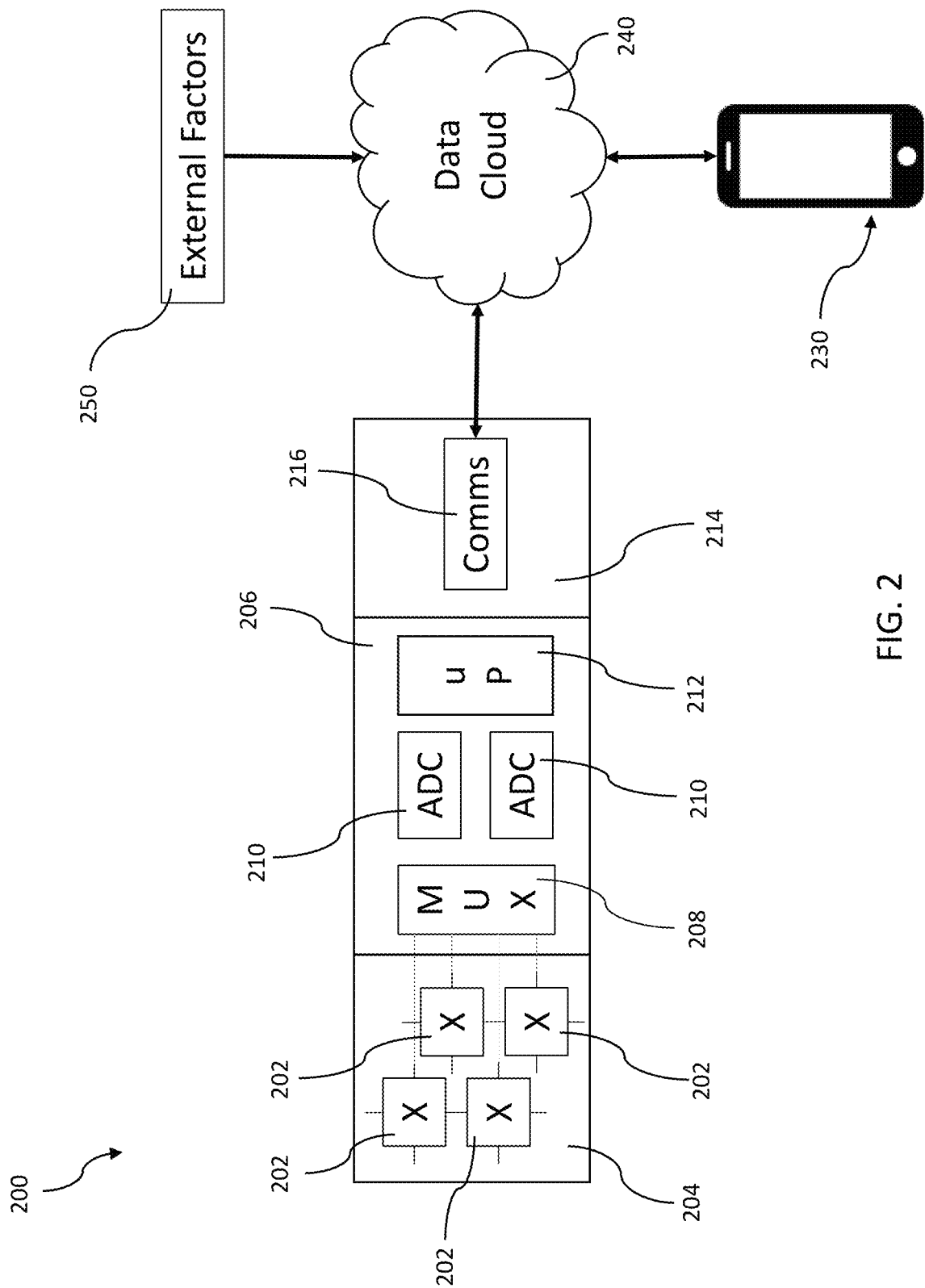
FIG. 2 illustrates a block diagram of one embodiment of a device including multiple sensing modalities that target multiple human or animal characteristics with a single circuit to measure, process, store, and communicate data.

The present invention uses multiple sensors, modalities, and/or targets through a single circuit, in a single device, with cross-modal (X-Mod) analytics. FIG. 2 illustrates a block diagram of one embodiment of a device 200 including multiple sensing modalities (e.g., image/photon, spectroscopy, electrochemical, inertial, thermal, RF, electromagnetic, ultrasound), that target multiple human or animal characteristics (e.g., skin temperature, sweat, tears, blood, urine, movement, pH, heart rate, blood oxygen levels) with a single circuit to measure, process, store, and communicate data. In one embodiment, the device 200 includes at least one environmental sensor to target environmental characteristics (e.g., temperature, air contaminants, sound) with the single circuit to measure, process, store, and communicate data. The device 200 includes at least two sensors 202 (e.g., four sensors 202) that form a biosensor array 204. In one example, the device 200 includes a heart rate sensor, a blood oxygen sensor, an accelerometer, and a temperature sensor. The device 200 includes an electronic core 206 that includes a multiplexer 208, at least one analog-to-digital converter (ADC) 210, and a microprocessor 212. The device 200 includes a flexible, replaceable communications flap 214 connected to the electronic core 206. The flexible, replaceable communications flap 214 includes at least one transceiver 216 that is operable to provide wireless network communication with at least one remote transceiver device 230. In one embodiment, the at least one transceiver 216 includes a coil, a radio frequency (RF) antenna, and/or a BLUETOOTH transceiver module.

In a preferred embodiment, the device 200 is controlled and configured (e.g., sample rate, sample frequency, sample instructions, processing instructions) via at least one remote transceiver device 230 (e.g., smartphone, tablet, laptop computer, desktop computer) with a user interface. The user interface is preferably a mobile application. The at least one remote transceiver device 230 is operable to process the data and send the data to an aggregated data cloud 240. The aggregated data cloud 240 is operable to further process the data and provide analytics. In one embodiment, the data is aggregated into a single cloud for linear modal processing of each modality. In another embodiment, the single cloud uses X-Mod analytics, which are cross-modal analytics that include change detection, rates, vectors, cross queues, tips, condition settings, user settings, self-calibrations, trends, patterns, validations, and/or alerts. Performance of the at least two sensors 202 is improved through active integration of the at least two sensors 202 into an array that is then processed, analyzed, stored, and accessed through a single system consisting of a measurement circuit, a mobile application, and a cloud database. The single circuit is designed for multiple sensors, signals, and sensitivities across many modalities. The single circuit isolates many different signals, filters noise, and mitigates interference across the modalities on the single circuit with highly complex firmware to handle each sensor read, sample rate, data scheme, storage, and other similar control commands. The aggregated data cloud 240 includes external factors 250, such as clinical observations, eyewitness data, offline analytics, laboratory test results, weather, social media analytics, external research, and web data. The analytics draw across all modalities and external information in the cloud 240.

Figure 3A:
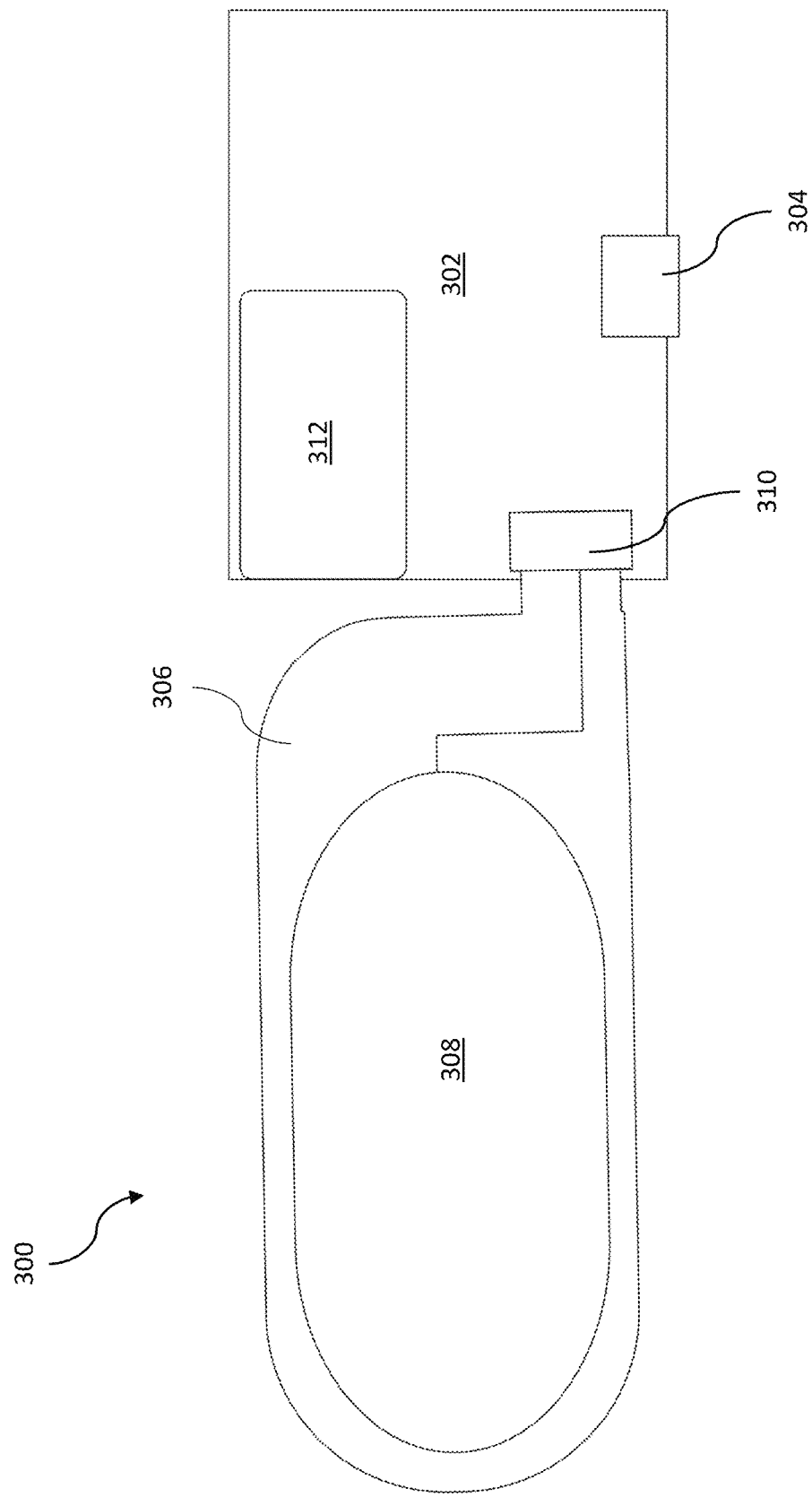
FIG. 3A illustrates a top perspective view of one embodiment of a device.

FIG. 3A illustrates a top perspective view of one embodiment of a device 300. The device 300 has an electronic core 302. In one embodiment, the electronic core 302 is formed of a polyimide substrate (e.g., Kapton®). The electronic core 302 is preferably flexible. In a preferred embodiment, the electronic core 302 includes at least one data port 304 (e.g., USB, micro-USB). The at least one data port 304 is preferably operable to recharge the at least one battery 310 via a cable connected to an alternating current (AC) power source. Additionally, a flexible, replaceable communications flap 306 is connected to the electronic core 302. In one embodiment, the flexible, replaceable communications flap 306 is formed of a polyimide substrate (e.g., Kapton®). The flexible, replaceable communications flap 306 includes at least one transceiver antenna 308 that is operable to provide wireless network communication with at least one remote transceiver device. In one embodiment, the at least one transceiver antenna 308 includes a coil. In an alternative embodiment, the at least one transceiver antenna 308 includes a radio frequency (RF) antenna. The at least one transceiver antenna 308 is connected to the electronic core 302 via an NFC connector 310. Additionally, or alternatively, the device includes at least one transceiver on the electronic core. The device 300 includes at least one battery 312 operable to power the device 300. In a preferred embodiment, the at least one battery 312 is a pouch type lithium-ion polymer battery. In one embodiment, the at least one battery 312 is a pouch type lithium-ion polymer battery, model FLPB352030 by Routejade. Alternative batteries are compatible with the present invention.

Figure 3B:
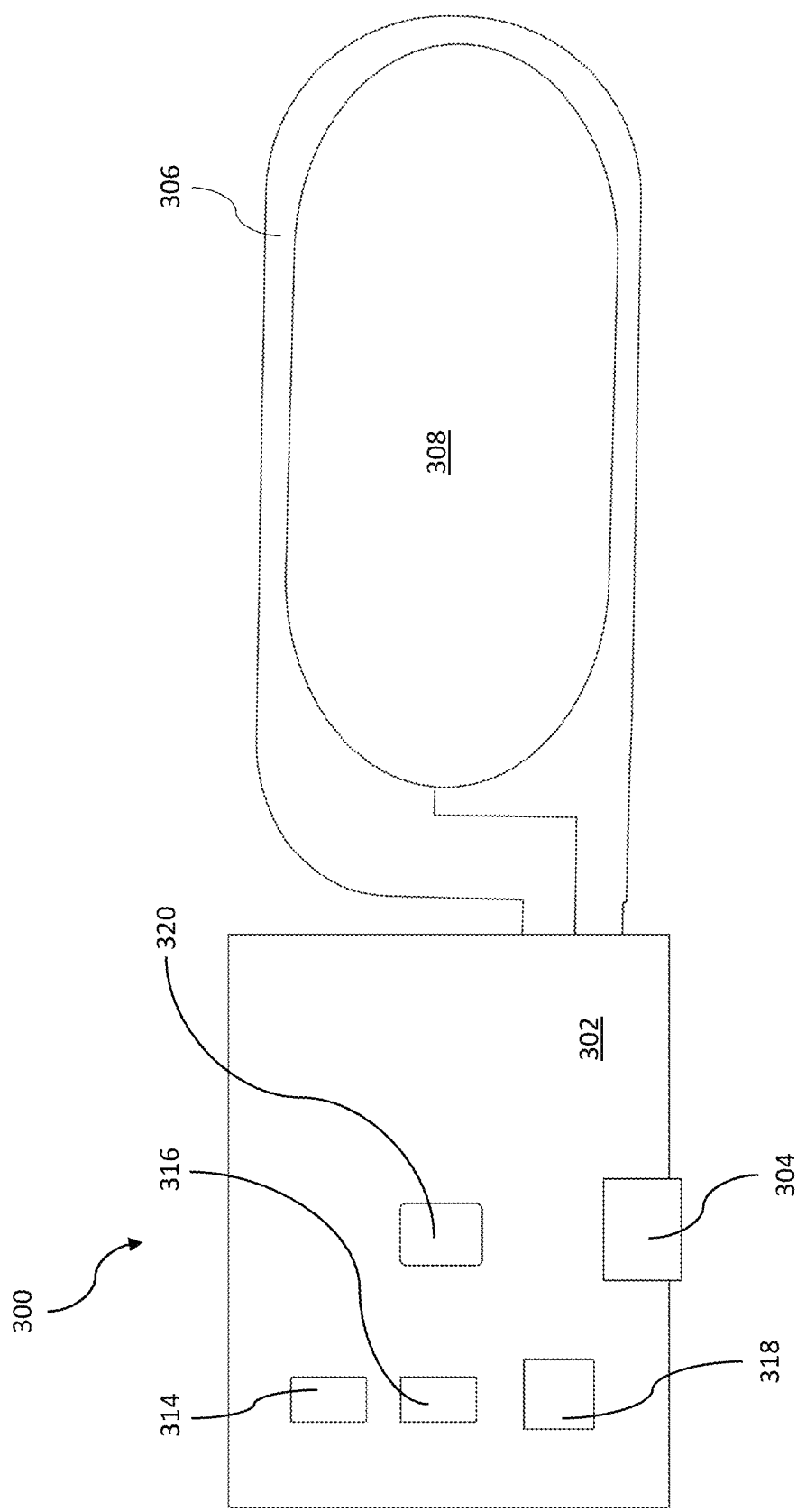
FIG. 3B illustrates a bottom perspective view of the device shown in FIG. 3A.

FIG. 3B illustrates a bottom perspective view of the device shown in FIG. 3A. The electronic core 302 includes at least one multiplexer 314, at least one analog-to-digital converter 316, and at least one processor 318. The at least one processor 318 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information. The electronic core 302 also includes an integrated blood oxygen sensor and heart rate monitor 320.

In another embodiment, the electronic core includes at least one memory. In one embodiment, the at least one memory is RAM, ROM, EPROM, EEPROM, and/or FLASH memory. In another embodiment, one or more of the at least one memory is incorporated into the at least one processor. In yet another embodiment, one or more of the at least one memory is operable to store raw data obtained by the device and/or at least one output datum calculated by the device.

In another embodiment, the electronic core includes at least one light emitting diode (LED). In one embodiment, the at least one LED is a tri-color LED. In one example, the tri-color LED is a red, green, and blue (RGB) LED. Advantageously, the RGB LED allows for color mixing, which allows for a greater number of colors from a single LED. One or more of the at least one LED is preferably operable to provide alerts based on analyzed data. In one example, an LED begins flashing (e.g., red flashing) when the analyzed data indicates that a user may experience an adverse event (e.g., heart attack) in the near future. In yet another embodiment, one or more of the at least one LED is operable to provide an indication of battery status. In one example, an LED begins flashing (e.g., white flashing) when the battery needs to be charged. In still another embodiment, one or more of the at least one LED is operable to provide an indication of the at least one memory status. In one example, an LED begins flashing (e.g., yellow flashing) when the at least one memory is almost full. This prompts the user to visit a scanner to refresh the at least one memory.

The device includes a sweat sensor, at least one temperature sensor, a pH sensor, a heart rate sensor, a blood oxygen sensor (e.g., a pulse oximetry sensor), an accelerometer, a glucose sensor, and/or at least one sympathetic nervous system (stress) sensor. In one embodiment, the sweat sensor measures a concentration of sodium in sweat and a concentration of potassium in sweat. The device is preferably operable to measure a concentration ratio of sodium to potassium, which provides an estimate of fluid losses (e.g., through sweat). The at least one temperature sensor is operable to measure skin temperature, core temperature, and/or ambient temperature. The accelerometer is operable to measure impact, shivering, seizures, and/or any other similar body movements. The blood oxygen sensor measures peripheral capillary oxygen saturation (SpO2). In one embodiment, the blood oxygen sensor is used in combination with an accelerometer measuring respiratory rates to produce sweat loss estimates using X-Mod analytics, which calibrates and/or validates prior readings from the sodium sensor and/or the potassium sensor. The at least one sympathetic nervous system (SNS) sensor is operable to measure cardio stress, pulmonary blood oxygen stress, physical stress, gastro stress, thermoregulation stress, glucose stress, arterial stress, and/or acid stress. In a preferred embodiment, the SNS sensor is non-invasive and uses at least one electrocardiogram (ECG) pad. In one embodiment, the SNS sensor is used to calibrate and/or validate other sensors. In a preferred embodiment, the glucose sensor is non-invasive and measures RF changes in the skin. The stabilized antibodies sensors detect the presence of designated antigens and other signs of bacterial and/or viral infections. In a preferred embodiment, viral sensors and/or bacterial sensors utilize antibodies stabilized through ionic fluid. This extends the shelf life of the viral sensors and/or the bacterial sensors under ambient/non-cooled storage conditions. The antibodies are used to detect antigens for designated infections using immunoassays and/or redox cells. In one embodiment, the assay results are presented as a binary true or false reading. A positive result indicating the presence of a target antigen is preferably represented visually (e.g., a color change to blue). Alternatively, the presence of a target antigen is indicated through voltage changes in a redox cell. In one embodiment, infection detection is further validated with detection signals from at least one electromagnetic sensor on the device. The at least one electromagnetic sensor is operable to detect at least one designated infection in the blood that carries a magnetic charge. In another embodiment, the device includes an analyte sensor to detect an analyte (e.g., hormones, electrolytes, small molecules (molecular weight<900 Daltons), proteins, metabolites). The device also includes modular communications (e.g., NEAR FIELD COMMUNICATION (NFC), BLUETOOTH, WI-FI, ZIGBEE).

As previously described, the at least one SNS sensor preferably uses at least one ECG pad. The at least one ECG pad is placed on a wrist, an upper arm, a chest, a back, a finger, a neck, or other designated location on a user. The at least one SNS sensor detects and processes sympathetic nerve system activity (SNSA). In one embodiment, changes in SNSA are correlated with known conditions, data from at least one other sensor, and external factors (e.g., clinical observations). The system is operable to distinguish between cardio stress, pulmonary blood oxygen stress, physical stress, gastro stress, thermoregulation stress, glucose stress, arterial stress, and/or acid stress via signal characterization (e.g., signal gain rate, signal amplitude shape, signal decline, signal phase shifts).

FIG. 4A illustrates a top perspective view of one embodiment of the invention as a wrist band. In one embodiment, the wrist band 400 is formed of neoprene. In another embodiment, the wrist band 400 houses the device from FIGS. 3A-3B. The wrist band 400 includes a first strap 402 and a second strap 404 with a piece of hook tape 406. A center pouch 406 is operable to hold the electronic core. The first strap 402 and the second strap 404 are affixed to the center pouch 410. In one embodiment, the center pouch 406 is secured using at least one snap, hook and loop tape, at least one tie, at least one magnetic closure, at least one clasp, at least one hole, at least one tab, at least one cord lock, and/or at least one buckle.

FIG. 4B illustrates a bottom perspective view of one embodiment of the invention as a wrist band. The first strap 402 includes a piece of loop tape 410. The piece of hook tape 406 and the piece of loop tape 410 are operable to secure the wrist band 400 to a wearer's wrist. Alternatively, the wrist band is operable to be secured to the wearer's wrist using at least one magnetic closure, at least one snap, at least one clasp, at least one tie, at least one hole, at least one tab, at least one cord lock, and/or at least one buckle. The center pouch 410 includes at least one opening 412 operable to allow at least one sensor to rest against the wearer's skin. In one example, the at least one sensor is an integrated blood oxygen sensor and heart rate monitor. In one embodiment, the center pouch 410 has an opening that is secured using hook and loop tape, at least one magnetic closure, at least one snap, at least one clasp, at least one tie, at least one hole, at least one tab, at least one cord lock. and/or at least one buckle. In another embodiment, the first strap and/or the second strap includes a pocket for the flexible, replaceable communications flap.

The device is operable to be charged using proximity charging with a wrist band pad. In a preferred embodiment, the proximity charging utilizes far-field technology that converts radio frequency (RF) energy into direct current (DC) power. In another embodiment, the wrist band includes a removeable power cable to recharge via an alternating current (AC) source.

In another embodiment, the device includes at least one medical textile. In one example, the device includes a top layer formed of a medical textile (e.g., 3M™ 9926T Tan Tricot Fabric Medical Tape), a bottom layer formed of a double-sided adhesive (e.g., 3M™ 9917 Medical Nonwoven Tape), and an electronic core positioned between the top layer and the bottom layer. The top layer formed of the medical textile includes an adhesive layer that is attached to a top side of the electronic core. The bottom layer formed of the double-sided adhesive is attached on a first side to a bottom side of the electronic core and intimately adhered on a second side to the skin of the wearer. In another example, the device includes a top layer formed of a medical textile (e.g., 3M™ 9926T Tan Tricot Fabric Medical Tape), a bottom layer formed of the medical textile (e.g., 3M™ 9926T Tan Tricot Fabric Medical Tape), and an electronic core positioned between the top layer and the bottom layer. The top layer formed of the medical textile includes an adhesive layer that is attached to a top side of the electronic core and the bottom layer formed of the medical textile includes an adhesive layer that is attached to a bottom side of the electronic core. In one embodiment, the top layer and/or the bottom layer includes at least one opening for a sensor, an LED, and/or other electronic components. In yet another embodiment, the device includes a transceiver antenna flap with a top layer formed of a medical textile (e.g., 3M™ 9926T Tan Tricot Fabric Medical Tape), a bottom layer formed of the medical textile (e.g., 3M™ 9926T Tan Tricot Fabric Medical Tape), and a transceiver antenna coil between the top layer and the bottom layer. Advantageously, this provides additional protection to the transceiver antenna coil. In one embodiment, the device is secured to the wearer using hook and loop tape, at least one magnetic closure, at least one snap, at least one clasp, at least one tie, at least one hole, at least one tab, at least one cord lock, and/or at least one buckle.

Figure 5:
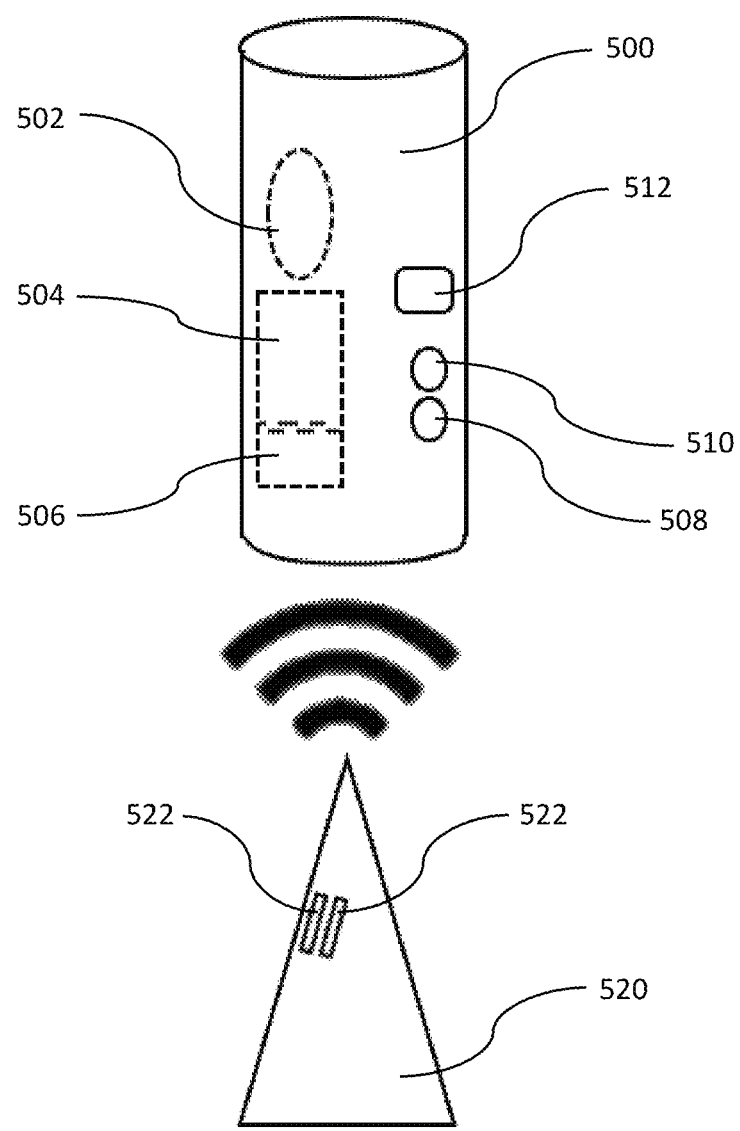
FIG. 5 illustrates one embodiment of the invention as a wearable forearm sleeve.

FIG. 5 illustrates one embodiment of the invention as a wearable forearm sleeve 500. In a preferred embodiment, the wearable forearm sleeve 500 is formed of neoprene and/or elastic. In one embodiment, the wearable forearm sleeve 500 is available in multiple sizes to accommodate different arm sizes (e.g., small, medium, large, child, infant). The wearable forearm sleeve 500 includes an antenna 502, flexible electronics 504 integrated into the sleeve, and a disposable sensor head 506. In one embodiment, the flexible electronics 504 include a multiplexer (MUX), at least one analog-to-digital converter (ADC), microprocessor (uP), a sensor array, GPS, and/or modular communications (e.g., WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication). In one embodiment, the sensor array includes a heart rate sensor, a blood oxygen sensor, a blood pressure sensor, an accelerometer, at least one temperature sensor, and/or a glucose sensor. The blood pressure sensor is an optical sensor in one embodiment. The disposable sensor head 506 includes at least one disposable sensor patch. In one embodiment, the at least one disposable sensor patch includes a sweat sensor, a sympathetic nervous system (SNS) sensor, a stabilized antibodies sensor (e.g., viral sensor, bacterial sensor), and/or a pH sensor. In a preferred embodiment, the device includes a power status indicator 508 that is visible on the exterior of the forearm sleeve. The device includes a sensor align button 510, which ensures that the connection between the sensor head and electronics in the sleeve are aligned and signals can flow, which is confirmed through a self-test of the microprocessor.

The wearable forearm sleeve 500 is operable to be charged using proximity charging with a sleeve recharging cone 520. In a preferred embodiment, the proximity charging utilizes far-field technology that converts radio frequency (RF) energy into direct current (DC) power. In one embodiment, the sleeve recharging cone 520 includes charging tabs 522 for contact charging as an alternative to proximity charging.

As previously described, the device includes a biosensor array. The device has a single multiplexer that pulls in signals from all of the sensors and all of the modalities. The signals flow through a series of capacitors and resistors to properly condition the signals, which are then converted using an ADC with a programmable amplifier. The amplifier gain is customized to reach designated thresholds for each sensor signal type, without over gain. The ADC signals are passed to the microprocessor for processing and converting, and then to storage in one or more of the at least one memory. The microprocessor manages read times, gains, processing, and store instructions. Data in storage is extracted via a communications event (e.g., NFC scan, BLUETOOTH read, burst).

A first source of data is the biosensor array, which is operable to sense multiple targets (e.g., sweat, urine, blood, skin, air, sound) using multiple modalities (e.g., imaging, spectroscopy, electrochemical, thermal). The integrated sensor array uses one circuit to measure, process, and store data. The circuit is designed for multiple sensors, signals, and sensitivities across many modalities. The single circuit isolates many different signals, filters noise, and mitigates interference across the modalities on the single circuit with highly complex firmware. A second source of data is external information, such as clinical observations, eyewitness data, offline analytics, laboratory test results, and web data. The data is aggregated into a single data cloud for linear modal processing of each modality. Cross modal analytics (X-Mod) include cross queues, tips, condition settings, user settings, self-calibrations, personalization, trends, patterns, validation of the data, and/or alerts based on the data. This results in a personal profile and situation profiles that are monitored and compared to an existing profile for a user and common demographic populations or other groups of common interest and/or attributes. Examples of groups of common interest and/or attributes include, but are not limited to, pregnancy, maternal delivery, cancer detection, cancer treatment, drug therapies, military special operations, emergency service personnel (e.g., fire, rescue, police), and athletes (e.g., race car drivers, football players, marathon runners).

One example of personalization is adjusting a blood pressure range based on patient history and/or conditions. For example, a blood pressure of 144/95 mmHg is deemed normal for a patient when the patient's blood sugar is under 200 mg/dL and an alert condition is set when the systolic blood pressure is above 150 when the patient's blood sugar is above 225 mg/dL. Advantageously, the personal profile is operable to adjust a baseline and at least one alert threshold, which prevents the system from needlessly alerting health and/or aid workers for conditions normal for a particular patient.

In a preferred embodiment, a mobile application on at least one remote transceiver device provides visibility to raw data and/or X-Mod analytics. The mobile application preferably is operable to provide an alert, a notification, and/or an acknowledgement. In one embodiment, the mobile application is operable to forward an alert, a notification, and/or an acknowledgement to another user. In one example, an alert regarding a patient is sent to a healthcare provider or a caregiver. In another example, a patient sends an acknowledgement after a healthcare provider makes a modification to a protocol (e.g., modification of insulin dosage, timing of medication). The mobile application preferably aligns information from the ISA with advisor prescribed information to recommend an action to a user.

In one embodiment, the mobile application provides a record and/or a timestamp for when a user completes an action (e.g., takes a medication). Additionally, or alternatively, the mobile application allows a user to mark an action as complete. In another embodiment, the mobile application allows a user to mark an action as delayed. The mobile application preferably resends a notification to remind the user to complete the delayed action.

In one embodiment, the mobile application includes at least one scheduled advisory action (e.g., dietary, exercise, medication) for a patient. A medication scheduled advisory action includes a name of a prescription, a dosage of the prescription (e.g., volume, weight), a prescription number, a production identification, and/or a picture reminder. In a preferred embodiment, the mobile application coordinates re-ordering consumables (e.g., medication, bandages). The mobile application preferably checks for potential drug interactions. In another embodiment, the mobile application advises a user of expectations and/or possible side effects based on a medication prescribed and/or a location. The mobile application interacts with healthcare providers (e.g., doctors, nurses, in-home health care), caregivers, hospice, and/or emergency services (e.g., paramedics, police, fire, first responders). In one embodiment, the mobile application is operable to be programmed for areas of concern, special medical treatment, and/or allergies. In another embodiment, the mobile application is operable to follow an escalation process of communication and alerts defined by a user and/or an advisor (e.g., healthcare provider).

In one embodiment, the mobile application records a time and a unit related to food (e.g., type, weight, calories, macros) and/or drink (e.g., by volume) consumed. The mobile application preferably records a physical activity of the user. In one embodiment, the physical activity of the user is measured by the accelerometer. In another embodiment, the mobile application records environmental parameters (e.g., temperature, humidity) of a location of the user.

In one embodiment, more than one mobile application is used to provide additional layers of security. In one example, a user has access to all health data of the user through a first mobile application, while the health data is inaccessible to a worker employed to read or scan sensor outputs through a second mobile application. Alternatively, the mobile application provides several account types. In one example, the mobile application includes a user (e.g., patient) account type, an employee (e.g., scanner) account type, a humanitarian (e.g., Red Cross) account type, and a healthcare provider (e.g., doctor, nurse) account type. In another example, authentication and/or encryption is used to provide for select user or restricted access to the health data of the individual.

Figure 6A:
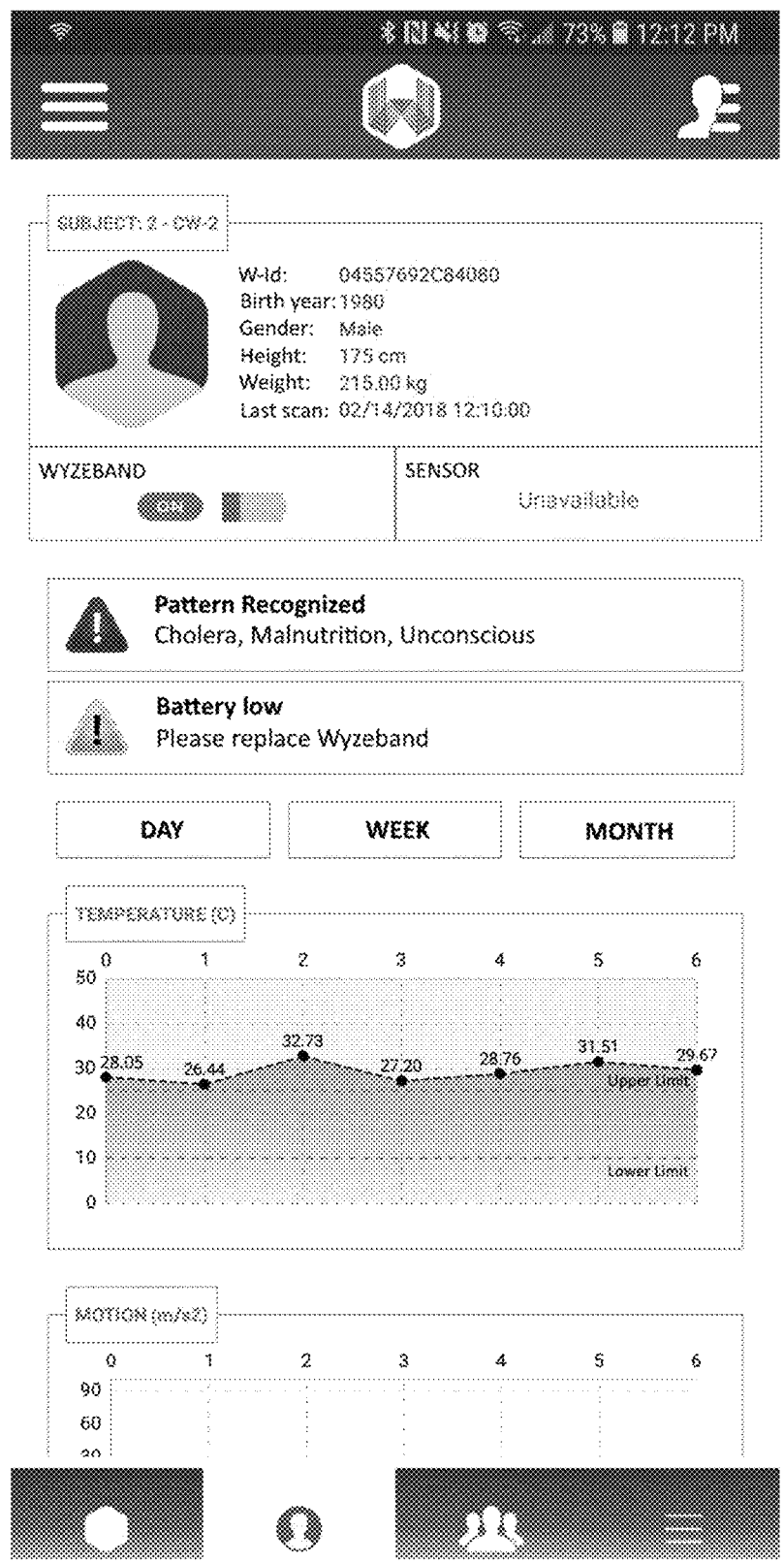
FIG. 6A illustrates one example of a user interface for a mobile application.

FIG. 6A illustrates one example of a user interface for a mobile application. The mobile application is accessible from a smartphone or tablet. Alternatively, or additionally, the mobile application is accessible on any portable (e.g., laptop computer) or desktop device via a cloud web application. The mobile application is operable to run on a single device or a plurality of devices concurrently. In one embodiment, the data can be accessed through a single mobile application. The mobile application sets configurations, processes data, transmits data, and retrieves data from the cloud, and presents data to users in a personalized graphical display. The mobile application is a multi-resource analyzer and assistant. The mobile application reminds users to take pre-determined actions or advisor actions resulting from real time data, profiles, and/or alerts. Advisors augment actions with detailed descriptions, such as a reminder to take a prescribed medicine including an amount and type of medication (e.g., pill). Using a reminder system, the mobile application is operable to track when the user completed an action and monitor how the action affects the user's profile. The mobile application uses data analytics to determine if the user is in a condition where an action needs to be taken to optimize at least one goal (e.g., wellness, performance) or minimize at least one risk. The mobile application detects when a user is unresponsive based on cross-modality change detections (e.g., no movement, low respiratory rate, low pulse) and is operable to trigger an automatic message to a user defined contact list or an emergency response service.

In the example shown in FIG. 6A, the user interface includes an identification number (W-Id), a birth year, a gender, a height, a weight, and a time of a last scan of a user. The user interface indicates whether the device is on or off. Additionally, the user interface displays a battery level. In this example, the battery level is low and the user interface displays a warning to replace the device. The user interface displays if any patterns are recognized based on the ISA data and/or the X-FAX. In this example, the user interface displays warnings for cholera, malnutrition, and unconsciousness. A temperature graph is shown on the user interface. The user interface is operable to display a motion graph.

Figure 6B:
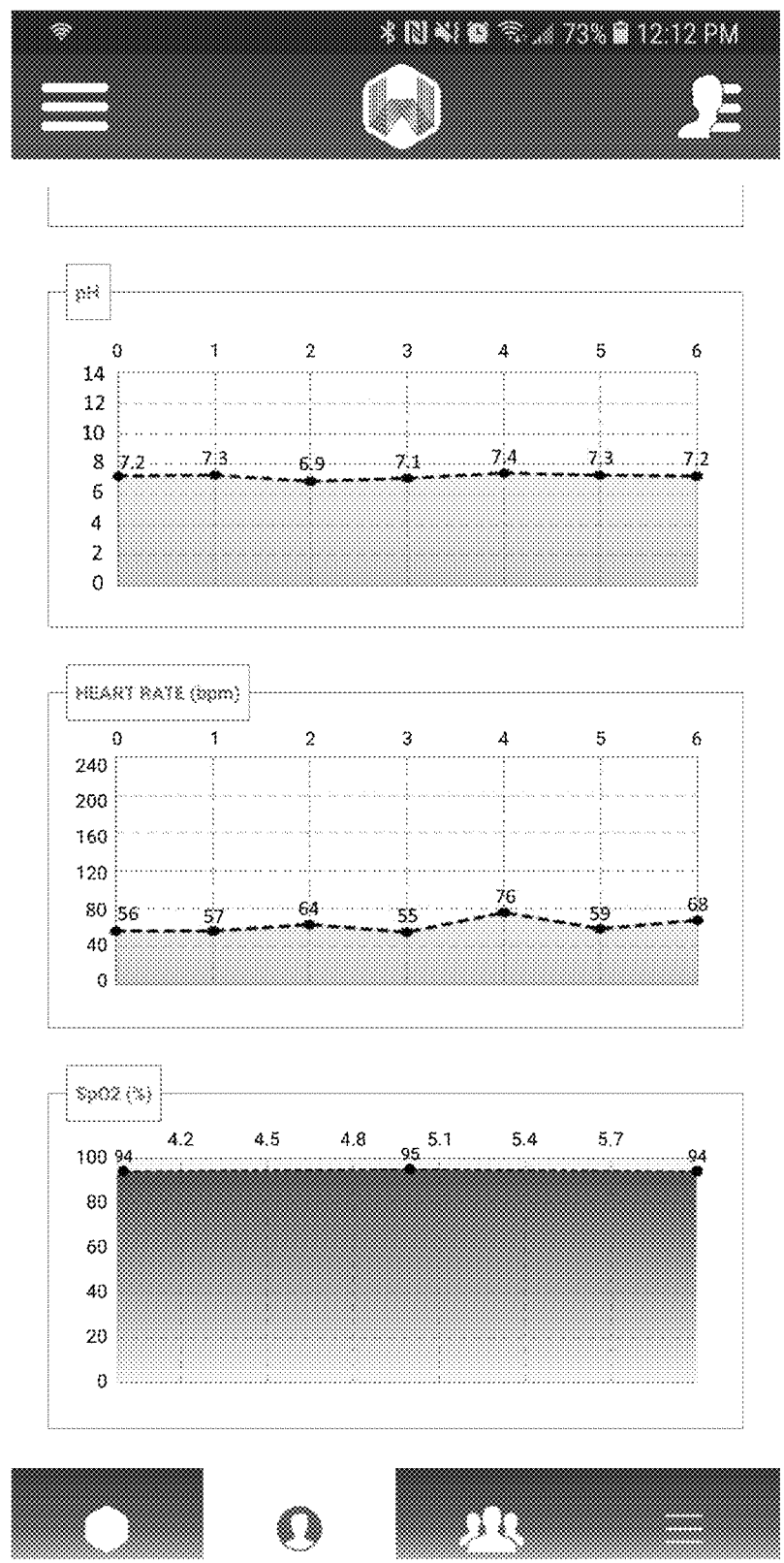
FIG. 6B illustrates another example of a user interface for a mobile application.

FIG. 6B illustrates another example of a user interface for a mobile application. In the example shown in FIG. 6B, the user interface displays a pH graph, a heart rate graph, and a blood oxygen level graph.

FIG. 7A is a quadrant diagram for estimating fluid and sodium replacement rates from Taylor et al., Regional variations in transepidermal water loss, eccrine sweat gland density, sweat secretion rates and electrolyte composition in resting and exercising humans, published in Extreme Physiology & Medicine, 2013; 2:4, doi:10.1186/2046-7648-2-4, which is incorporated herein by reference in its entirety. As shown in FIG. 7A, oxygen consumption increases linearly with increases in heart rate due to exercise. Therefore, starting with the heart rate (labeled "1" in the figure), an oxygen consumption is approximated (labeled "2" in the figure). Additionally, core body temperature is linked to oxygen consumption. Thus, the core body temperature is approximated (labeled "3" in the figure). Sweat rate increases asymptotically relative to core temperature. Therefore, the sweat rate is approximated (labeled "4" in the figure). Finally, sweat sodium secretion is a positive linear function of sweat rate, allowing for an approximation of the sweat sodium secretion (labeled "5" in the figure) and fluid replacement rates (labeled "6" in the figure) required to maintain body-fluid and electrolyte homeostasis.

As previously described, the present invention utilizes X-Mod schemes to improve accuracy via multi-source calibration and validation. X-Mod analytics use changes in multiple sensor streams and create profiles based on change rates, change vectors, change trends, and/or change patterns. A collection of changes that represent a normal day for an individual is called a personal profile. Similarly, a set of changes that characterize a unique situation for a group and/or demographic of a population all under a similar situation (e.g., pregnancy, cancer, concussion) is called a situation profile. Personal profiles and situation profiles are compared to real time biosignature change activity in a user to detect anomalies, concerns, and/or general items of interest.

Figure 7B:
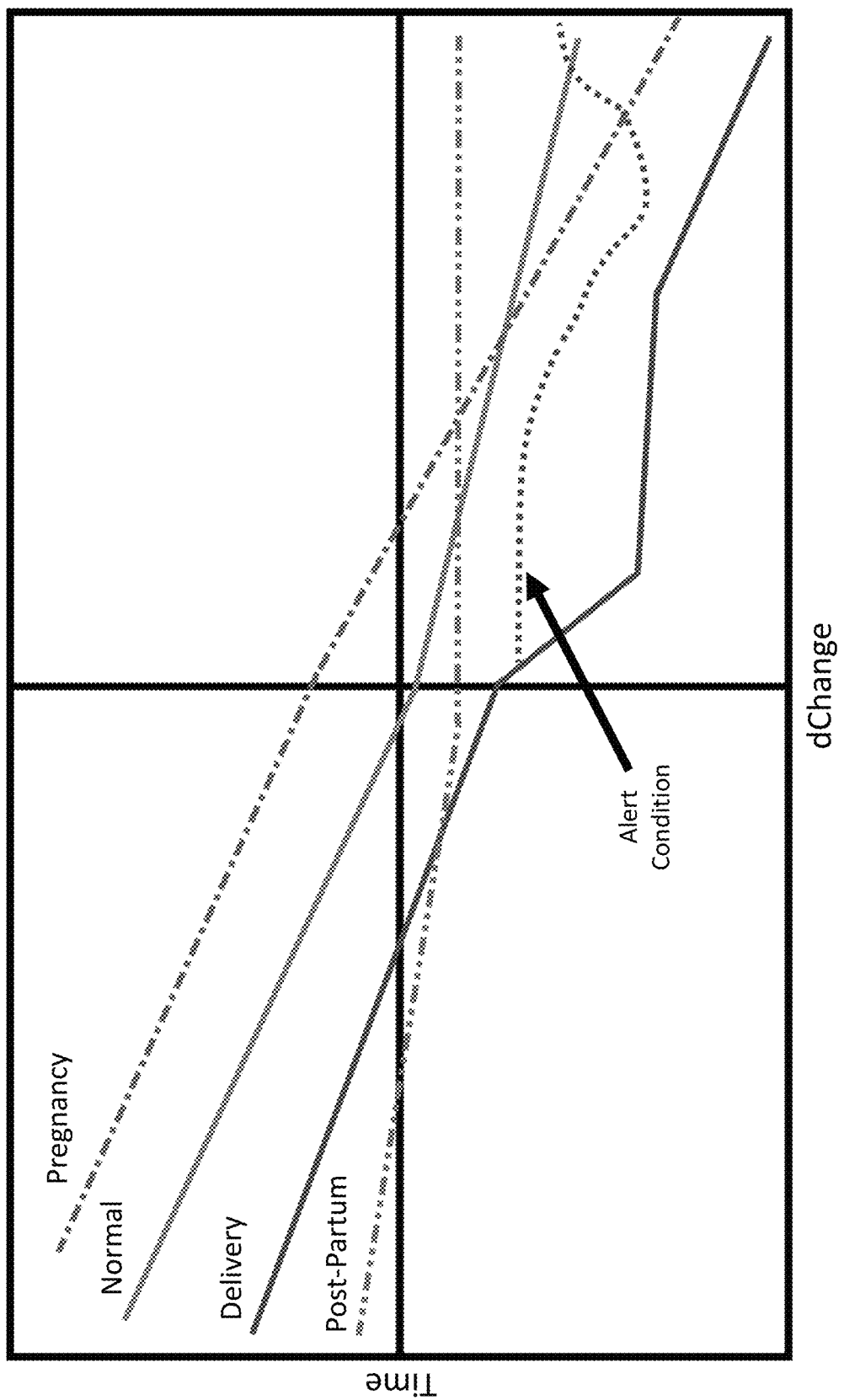
FIG. 7B illustrates a graph of situation profiles for normal patients, pregnant patients, patients during delivery, and post-partum patients.

FIG. 7B illustrates a graph of situation profiles for normal patients, pregnant patients, patients during delivery, and post-partum patients. In the example shown in FIG. 7B, a deviation of a patient from the situation profile for patients during delivery is shown with a dotted line. This deviation from the situation profile triggers an alert condition, allowing for closer supervision of the patient and/or medical intervention.

For the cross-modal (X-Mod) analysis, the following algorithm is used to determine a change in biosignature (dBioSig):

$$dBioSig = dS1 + dS2 + dS3 + \ldots + dSn$$

where dS is a biosensor change over a period of time (T). The biosensor change over the period of time (dS) is a function of a magnitude/scaling factor (m), sensor dependent variables (dSV), and time dependent variables (dTV).

One example of a change in biosignature is shown in the following equation:

$$dContraction = \frac{0.32 \times f(dHR) + f(dO2) + f(dAccel)}{f(dTemp) + f(dSLR)}$$

where dHR is a change in heart rate over a period of time, dO2 is a change in blood oxygen level over the period of time, dAccel is a change in acceleration over the period of time, dTemp is a change in body temperature over the period of time, and dSLR is a change in sodium loss rate over the period of time.

FIG. 8A illustrates one embodiment of a system for cloud biosignature analytics. Data from sensors and external factors are used to create biosignatures. A biosignature is a collection of biomarker changes (deltas) over time. In the example shown in FIG. 8A, biosignatures are shown for heart rate (dHR), body temperature (dT° F.), blood oxygen level (dSpO2), pH (dpH), and SNS activity (dSNS). The biosignature data is compared to personal profiles and situation profiles to determine if there is a deviation from an expected profile. In the example shown in FIG. 8A, deviations from the situation profile are shown for heart rate, body temperature, and SNS activity with the dashed lines. These deviations would trigger an alert, resulting in closer supervision of the patient and/or medical intervention.

Figure 8B:
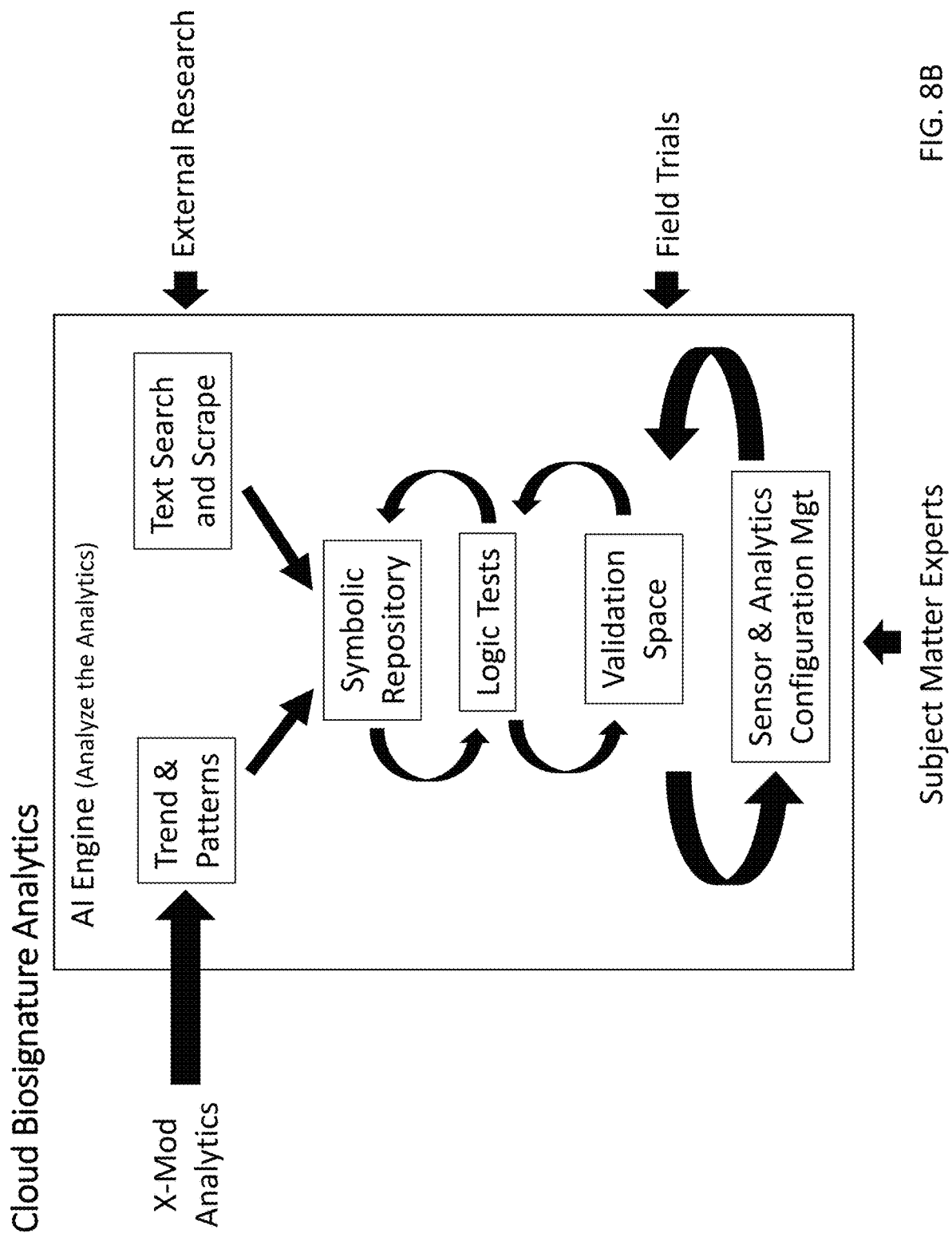
FIG. 8B illustrates a block diagram of an artificial intelligence engine for analyzing cross-modal analytics.

The X-Mod analytics are transmitted to an artificial intelligence (AI) engine to analyze the X-Mod analytics as shown in FIG. 8B. The AI engine examines the X-Mod analytics for trends and/or patterns. Further, the AI engine incorporates external research and is operable to perform text searches and/or scrapes of the external research. The trends and/or patterns and the text searches and/or scrapes of the external research are sent to a symbolic repository. Logic tests are performed on the data in the symbolic repository and then the results of the logic tests are validated. The validated results are used to perform sensor and analytics configuration management, which enhances accuracy of data results. The AI engine also incorporates field trials and/or subject matter experts to further analyze the X-Mod analytics.

Figure 9A:
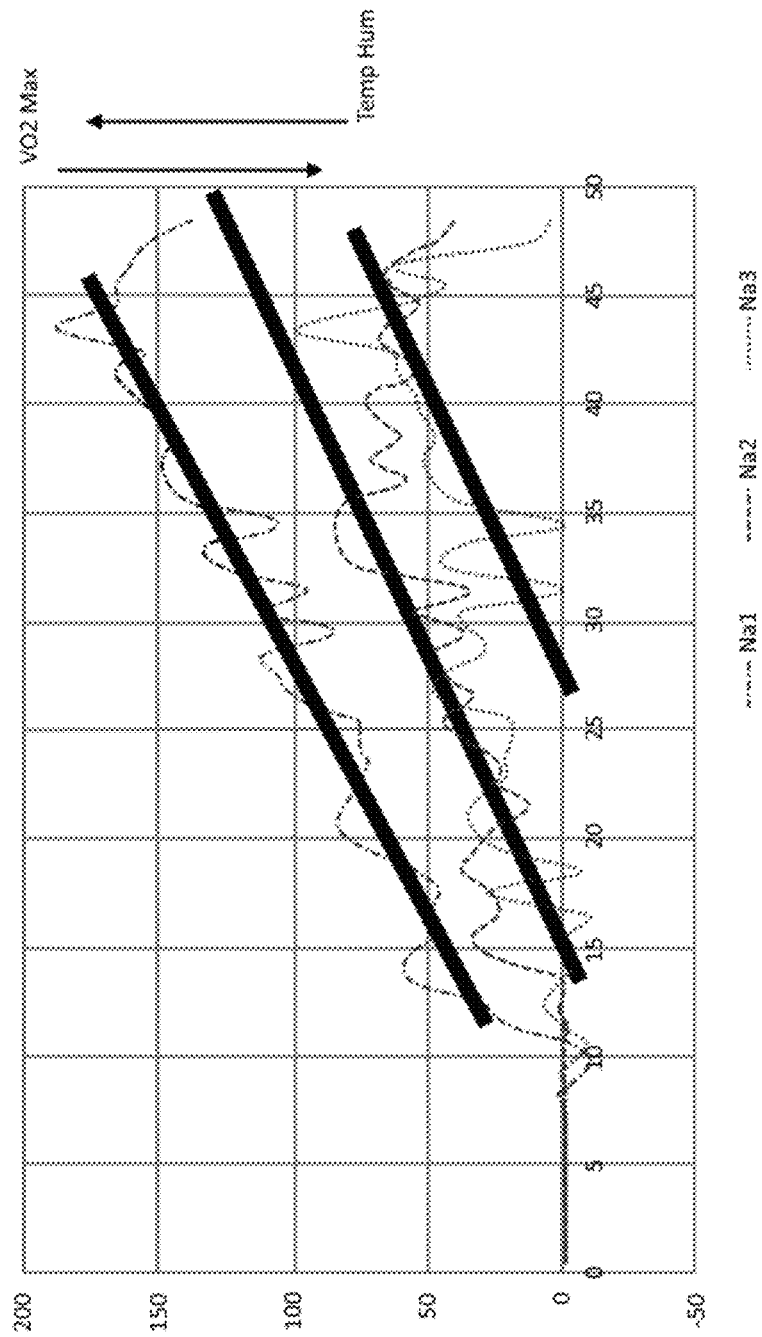
FIG. 9A illustrates data from an electrochemical sensor with an ion selective electrode that yields a signal strength that corresponds to sodium ion concentration in sweat.
Figure 9B:
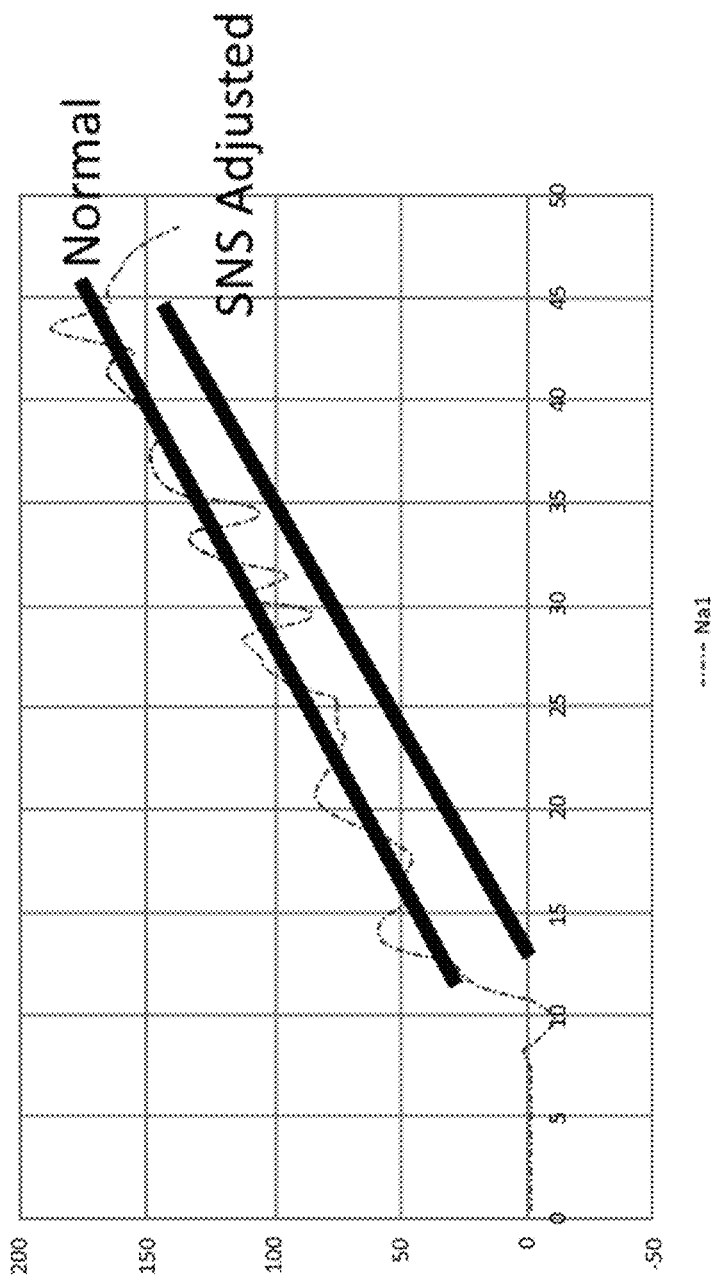
FIG. 9B illustrates data from the electrochemical sensor in FIG. 9A calibrated using sympathetic nervous system activity.

FIGS. 9A-9B illustrates the improvements in accuracy due to integrated sensor arrays. FIG. 9A illustrates data from an electrochemical sensor with an ion selective electrode (ISE) that yields a signal strength that corresponds to sodium ion concentration in sweat, which is in turn an indicator of instantaneous local sweat rate. If calibrated, the ISE signal can reflect real-time sweat loss (fluid) and sodium (electrolyte) loss. When tracked over time, the signal can help athletes know how much fluid and electrolytes have been lost and need to be replenished to maintain or optimize performance.

However, calibrating a signal to determine sweat (fluid) loss is difficult because a human body is very adaptable to stress. When stressed by ambient temperature, humidity, and other similar factors, sodium secretion into sweat is conserved, resulting in a much higher sweat rate (fluid loss) at a given sodium concentration in order to accelerate cooling. Additionally, variations in conditioning level (VO$_2$ max) further complicate the calibration, and introduce additional variability into the results. Consequently, external factors (e.g., heat, humidity) and conditioning induced stress will cause the sweat/sodium relationship curve to shift, meaning sodium is conserved so sweat volume actually increases with lower sodium concentration. This results in an incorrect original signal calibration. Many factors influence human sweat rate, which is a dynamic human body phenomenon that is difficult to model through software alone.

One method of measuring human physiological stress is by monitoring the human sympathetic nervous system (SNS). Sympathetic nervous system activity (SNSA) signals control physiological response to stress (fight or flight response), including the thermal regulation system (sweat glands). As a result, SNS signals are an ideal means to better calibrate an ISE sweat sensor signal as shown in the graph in FIG. 9B.

FIG. 10 shows one embodiment of an assessment table of an early warning system monitoring abnormal bio-activity. At least one algorithm uses a combination of biosignature change thresholds to detect various concerns. In a preferred embodiment, the rate of change determines the severity of the concern. The combination of at least one biosignature change and at least one rate of change of the at least one biosignature change triggers an alert. In a preferred embodiment, the alert is assigned a severity level (e.g., caution, alert, critical) based on the rate of change. In one embodiment, the severity level is assigned a color code (e.g., caution is assigned a yellow color, alert is assigned an orange color, and critical is assigned a red color). For example, a 25% change per minute in heart rate (dHR) is assigned a caution level (e.g., yellow color), a 50% change per minute in heart rate (dHR) is assigned an alert level (e.g., orange color), and a 75% change per minute in heart rate (dHR) is assigned a critical level (e.g., red color). The color-coded alerts allow users to manage massive, complex, and interrelated biosignatures for a plurality of individuals, by providing continual real-time situational awareness derived from the sensors and the cross-modality based alerts.

FIG. 11A shows a table of sensors that can be incorporated into the device and their associated biosignatures related to malaria. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects an increase in heart rate over a 1-2 day period due to a decrease in effective circulating volume (ECF). A blood oxygen sensor detects a normal blood oxygen level. A blood pressure sensor detects a decrease in blood pressure due to lower ECF. At least one SNS sensor detects an increase in at least one stress level (e.g., cardio stress, pulmonary blood oxygen stress, physical stress, gastro stress, thermoregulation stress, glucose stress, arterial stress, acid stress). A stabilized antibodies sensor detects a target antigen. In one embodiment, the device indicates a color change to blue to indicate the presence of the target antigen. A skin temperature sensor detects a decrease in skin temperature over several days as the body increases vasoconstriction and decreases sweat production in an attempt to maintain homeostasis. A sodium sensor detects an increase in sodium loss. A potassium sensor detects an increase in potassium loss. An accelerometer detects no significant diagnostic information early in the disease state. However, lethargy and decreases movement are likely to present if the patient is not treated. Clinical observations may include lethargy, loose stools, poor per os (PO) intake, and/or blood in the stools. Social media analytics are patient dependent.

FIG. 11B shows a table of sensors that can be incorporated into the device and their associated biosignatures related to myocardial infarction. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects an increase in heart rate due to pain, decreased cardiac output leading to a compensatory increase in heart rate, and a generation of arrhythmias depending on where the coronary occlusion has occurred. Occasionally, the heart rate sensor detects a decrease in heart rate due to specific conditions (e.g., sinoatrial (SA) ischemia, Bezold-Jarisch syndrome). A blood oxygen sensor generally detects a normal blood oxygen level. The blood oxygen sensor may detect a lower blood oxygen if there is a massive myocardial infarction (MI) leading to poor cardiac output and acute heart failure. A blood pressure sensor may detect an increase in blood pressure or a decrease in blood pressure. An acute MI can cause sympathetic stimulation leading to an increase in heart rate and, thus, an increase in blood pressure. Blood pressure is generally slightly lower than normal because cardiac output is usually lower than normal after a heart attack. At least one SNS sensor detects an increase in cardio stress. A skin temperature sensor detects a normal skin temperature or a slightly lower skin temperature. In cases where the skin temperature of distal extremities is noticeably decreased, this could be an indicator of cardiogenic shock and is an ominous sign. A sodium sensor detects a decrease in sodium levels during an acute myocardial infarction. Sodium levels remain low on day 1 and returns to normal by day 4. Improvement in serum sodium indicates better clinical outcomes. Studies assume this is due to increased permeability of the sarcolemma. A potassium sensor detects a decrease in potassium levels during an acute myocardial infarction. Potassium levels usually return to normal by day 3. Hypokalemia might be due to increased circulating catecholamines during and after an acute myocardial infarction. A pH sensor detects a normal pH or an abnormal pH depending on whether the heart is able to maintain distal perfusion. An accelerometer detects no significant diagnostic information. Clinical observations may include pain that radiates to the jaw, between the shoulder blades or on the back, and/or down the left arm. Patients sometimes complain of chest pressure or a burning sensation. Social media analytics may include the patient reporting a feeling of unwellness over several days.

FIG. 11C shows a table of sensors that can be incorporated into the device and their associated biosignatures related to alcohol poisoning. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. Changes in heart rate detected by a heart rate sensor due to drug use and/or overdose are drug dependent. For example, opioids (e.g., heroin) cause bradycardia in high doses. Sympathomimetics (e.g., phencyclidine (PCP), methamphetamine, cocaine) increase heart rate until the drug is metabolized, which is usually occurs in a time course of hours. A blood oxygen sensor detects a decreased blood oxygenation in opioid-like drugs. Changes in blood pressure detected by a blood pressure sensor are variable depending on co-morbid conditions with drug use (e.g., hydration status, energy status, cardiac function). For example, sympathomimetics (e.g., cocaine) generally increase blood pressure for several hours. The half-life of cocaine with normal liver and function is 60 minutes. A SNS sensor detects an increase in gastro stress and/or arterial stress. Changes in skin temperature, sodium level, potassium level, glucose level, and pH as detected by a skin temperature sensor, a sodium sensor, a potassium sensor, a glucose sensor, and a pH sensor, respectively, are variable. Changes in acceleration as detected by an accelerometer are variable depending on drug intake. Drugs that cause limbic dissociation (e.g., PCP) and/or sympathomimetics (e.g., methamphetamine) may cause changes in acceleration. Further, patients may exhibit increased motor movement due to hallucinations and/or rage. Clinical observations may include decreased check ins due to drug use or addiction, poor activities of daily living, a disheveled appearance, signs of intoxication (e.g., rage), inability to sustain a conversation, and/or poorly coordinated motor function. Social media analytics are variable.

FIG. 11D shows a table of sensors that can be incorporated into the device and their associated biosignatures related to drug use and/or overdose. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. Changes in heart rate detected by a heart rate sensor due to drug use and/or overdose are drug dependent. For example, opioids (e.g., heroin) cause bradycardia in high doses. Sympathomimetics (e.g., phencyclidine (PCP), methamphetamine, cocaine) increase heart rate until the drug is metabolized, which is usually occurs in a time course of hours. A blood oxygen sensor detects a decreased blood oxygenation in opioid-like drugs. Changes in blood pressure detected by a blood pressure sensor are variable depending on co-morbid conditions with drug use (e.g., hydration status, energy status, cardiac function). For example, sympathomimetics (e.g., cocaine) generally increase blood pressure for several hours. The half-life of cocaine with normal liver and function is 60 minutes. A SNS sensor detects an increase in gastro stress and/or arterial stress. Changes in skin temperature, sodium level, potassium level, glucose level, and pH as detected by a skin temperature sensor, a sodium sensor, a potassium sensor, a glucose sensor, and a pH sensor, respectively, are variable. Changes in acceleration as detected by an accelerometer are variable depending on drug intake. Drugs that cause limbic dissociation (e.g., PCP) and/or sympathomimetics (e.g., methamphetamine) may cause changes in acceleration. Further, patients may exhibit increased motor movement due to hallucinations and/or rage. Clinical observations may include decreased check ins due to drug use or addiction, poor activities of daily living, a disheveled appearance, signs of intoxication (e.g., rage), inability to sustain a conversation, and/or poorly coordinated motor function. Social media analytics are variable.

FIG. 11E shows a table of sensors that can be incorporated into the device and their associated biosignatures related to diarrheal diseases. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects an increase in heart rate over a 1-2 day period due to a decrease in effective circulating volume (ECF). A blood oxygen sensor detects a normal blood oxygen level. A blood pressure sensor detects a decrease in blood pressure due to lower ECF. At least one SNS sensor detects an increase in at least one stress level (e.g., cardio stress, pulmonary blood oxygen stress, physical stress, gastro stress, thermoregulation stress, glucose stress, arterial stress, acid stress). A stabilized antibodies sensor detects a target antigen. In one example, the device indicates a color change to blue. A skin temperature sensor detects a decrease in skin temperature over several days as the body increases vasoconstriction and decreases sweat production in an attempt to maintain homeostasis. A sodium sensor detects an increase in sodium loss. A potassium sensor detects an increase in potassium loss. An accelerometer detects no significant diagnostic information early in the disease state. However, lethargy and decreases movement are likely to present if the patient is not treated. Clinical observations may include lethargy, loose stools, poor PO intake, and/or blood in the stools. Social media analytics are patient dependent.

FIG. 11F shows a table of sensors that can be incorporated into the device and their associated biosignatures related to a fight. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects an increase in heart rate due to fight or flight syndrome. A blood oxygen sensor detects a normal blood oxygen level or a slight increase in blood oxygen level. A blood pressure sensor detects an increase in blood pressure due to fight or flight syndrome. An SNS sensor detects an increase in gastro stress. A skin temperature sensor likely detects an increase in skin temperature due to an increase in sweating due to an increase in metabolic rate. A sodium sensor detects a normal sodium level. A potassium sensor detects a normal potassium level. A glucose sensor detects a glucose level within normal limits or a slightly increased glucose level due to fight or flight (catabolism and glycogenolysis), but the effect will be delayed. A pH sensor detects a normal pH. An accelerometer detects significant vector changes during the fight. Clinical observations may include signs of combat, such as hematomas in likely areas (e.g., arms, face, eyes, mouth) and/or broken ribs. Social media analytics are patient dependent.

FIG. 11G shows a table of sensors that can be incorporated into the device and their associated biosignatures related to measles. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor may detect an increase in baseline heart rate. In one example, the heart rate is increased if the patient is dehydrated from diarrhea and/or emesis. A blood oxygen sensor detects a normal blood oxygen level. A blood pressure sensor may detect a lower blood pressure in patients who are dehydrated due to diarrhea and/or emesis. A SNS sensor detects an increase in gastro stress. A stabilized antibodies sensor detects a target antigen. In one example, the device indicates a color change to blue. A skin temperature sensor detects an increase in skin temperature. For example, an initial sign of measles is often a high fever (e.g., above 104° F.) that typically lasts 4-7 days. A sodium sensor may detect an increase in sodium loss in patients who are dehydrated due to diarrhea and/or emesis. A potassium sensor may detect an increase in potassium loss in patients who are dehydrated due to diarrhea and/or emesis. A glucose sensor detects no noticeable changes in glucose level. A pH sensor may detect an alkalotic level in patients who are dehydrated due to diarrhea and/or emesis. An accelerometer detects no significant diagnostic information. Clinical observations may include malaise and/or anorexia associated with decreased activity. The prodromal phase lasts 7-14 days before fever begins. Social media analytics may include complaints related to a typical rash seen with viral diseases. However, measles is mostly a viral illness that affects children.

FIG. 11H shows a table of sensors that can be incorporated into the device and their associated biosignatures related to acute respiratory infections (flu). In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects a normal heart rate or an increased heart rate due to an inflammatory response to the disease and/or hypoxia due to an infected lung. A blood oxygen sensor detects a normal blood oxygen level or a decreased blood oxygen level depending on the severity of the disease. A blood pressure sensor will likely detect a normal blood pressure unless the infection is causing a systemic inflammatory response and, thus, decreases blood pressure. A SNS sensor detects an increase in pulmonary stress. A stabilized antibodies sensor detects a target antigen. In one example, the device indicates a color change to blue. A skin temperature sensor detects an increase in skin temperature, a normal skin temperature, or a decrease in skin temperature depending on a degree of infection and a stage of infection. A sodium sensor detects no noticeable change in sodium level. A potassium sensor detects no noticeable change in potassium level. A glucose sensor detects a normal glucose level or an increased glucose level depending on the degree of infection and the stage of infection. A pH sensor detects a normal pH level or a decreased pH level depending on a degree of infection and a stage of infection. An accelerometer detects no significant diagnostic information. Clinical observations may include a normal appearance (early stages) or a very sick appearance with signs such as increased sweating, an increased respiratory rate, shortness of breath with minimal exertion, febrile seizures, and/or a productive cough that may or may not be associated with blood. Social media analytics are patient dependent.

FIG. 11I shows a table of sensors that can be incorporated into the device and their associated biosignatures related to malnutrition. In one example, the device includes a heart rate sensor, a blood oxygen sensor, a blood pressure sensor, at least one SNS sensor, a stabilized antibodies sensor, a skin temperature sensor, a sodium sensor, a potassium sensor, a glucose sensor, a pH sensor, and/or an accelerometer. A heart rate sensor detects an increased heart rate during the initial phase of malnutrition and a decreased heart rate as energy stores begin to deplete. In advanced states of protein loss, a patient may have poor breathing and/or ventilatory function as detected by a blood oxygen sensor due to loss of intercostal and diaphragmatic muscle mass. This will lead to hypoxia and hypercarbia. A few studies have shown that malnourished children tend to have an increased blood pressure compared to control groups. Alternatively, in extreme conditions, poor heart function due to poor vitamin intake (e.g., Vitamin B1, also known as thiamine, which is a co-enzyme needed for proper cardiac muscle and nerve function) due to decreased stroke volume and bradycardia will cause a low blood pressure. Additionally, poor albumin and/or protein intake will lower effective circulating volume, also contributing to a lower blood pressure. A SNS sensor detects an increase in gastro stress. A skin temperature sensor detects a decrease in skin temperature over time as immune function and metabolism are negatively affected due to decreased protein and/or vitamin intake. The ability to maintain a normal body temperature will worsen. A sodium sensor generally detects a lower serum sodium concentration due to an overabundance of free water compared to sodium level, even though the patient has a sodium overload. The serum sodium concentration will also decrease to diarrhea. A potassium sensor detects a lower total body potassium due to decreased intake and poor muscle mass. Most serum levels are subclinical; however, in overt malnourished cases or concomitant diarrhea the serum level will be low. The mean fasting blood glucose level as detected by a glucose sensor is generally lower in malnourished children is lower compared to controls. The pH as measured by a pH sensor depends on the ability of hate kidneys to maintain a bicarbonate buffer. However, as cardiac output decreases, renal function will worsen and retention of free water will increase. This will dilute plasma electrolytes, which may lead to a decreased pH level. Hypercarbia from poor ventilatory function will increase blood serum activity. An accelerometer detects no significant diagnostic information. Clinical observations may include a gaunt appearance, a loss of muscle mass, and jaundice. Loss of energy or activity are common symptoms. Decreased gastrointestinal use will lead to gut wasting and bacterial translocation, thus leading to sepsis. As a note, the prevalence of malnutrition in hospitals around the world is up to 50%. Social media analytics are patient dependent.

Figure 12:
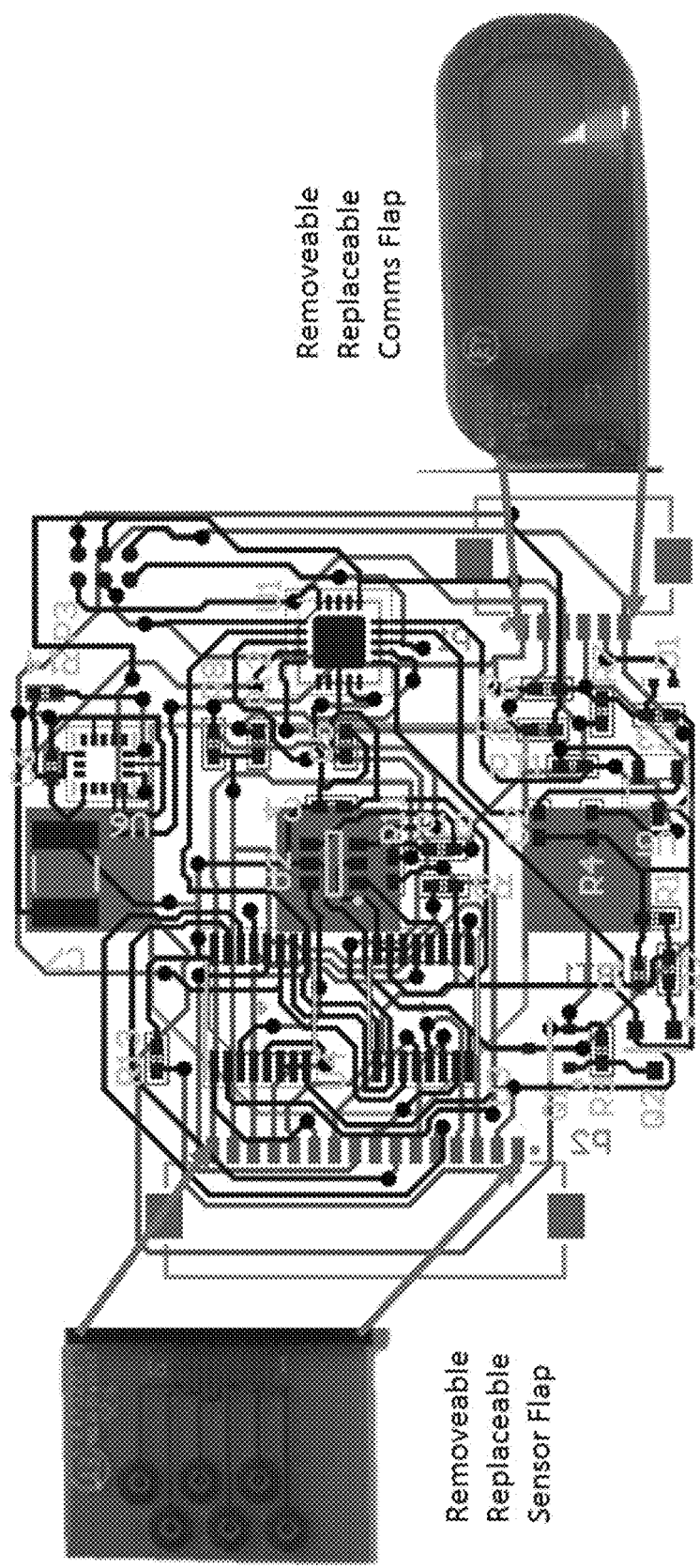
FIG. 12 illustrates a core layout of an embodiment of the device including a flexible, replaceable sensor flap.

FIG. 12 illustrates a core layout of an embodiment of the device including a flexible, replaceable sensor flap. The device has an electronic core including at least one multiplexer, at least one analog-to-digital converter, and at least one microprocessor. A flexible, replaceable sensor flap is connected to the electronic core. The flexible, replaceable sensor flap includes at least one sensor. In one embodiment, the at least one sensor is a sweat sensor, a sympathetic nervous system sensor (stress sensor), a stabilized antibodies sensor, and/or a pH sensor. In one embodiment, the at least one sensor includes at least one ion-selective electrode (ISE). In one embodiment, the ISE includes an ionophore polymer coating. Additionally, a flexible, replaceable communications flap is connected to the electronic core. The flexible, replaceable communications flap includes at least one transceiver antenna that is operable to provide wireless network communication with at least one remote transceiver device. In one embodiment, the transceiver antenna is a coil. In an alternative embodiment, the transceiver antenna is a radio frequency (RF) antenna. In one embodiment, the flexible, replaceable sensor flap and/or the flexible replaceable communications flap are connected to the electronic core via a zero insertion force (ZIF) connector. Advantageously, the flexible, replaceable sensor flap and the flexible, replaceable communications flap allow for upgrading sensors and communications without replacing the electronic core. This allows the device to be modified for particular conditions and/or mission needs. For example, a device can be upgraded to include a stabilized antibodies sensor following a disease outbreak without replacing the entire device.

In one embodiment, the device is an ear sensor. In one example, the ear sensor includes a heart rate sensor, a blood oxygen sensor, a blood pressure sensor, at least one temperature sensor (e.g., skin temperature, core temperature, ambient temperature), and/or a motion sensor (e.g., accelerometer). In another embodiment, the device is a patch. In one example, the patch includes a sweat sensor to monitor at least one analyte (e.g., sodium, potassium, cortisol), at least one temperature sensor (e.g., skin temperature, core temperature, ambient temperature), and/or a motion sensor (e.g., accelerometer).

Figure 13A:
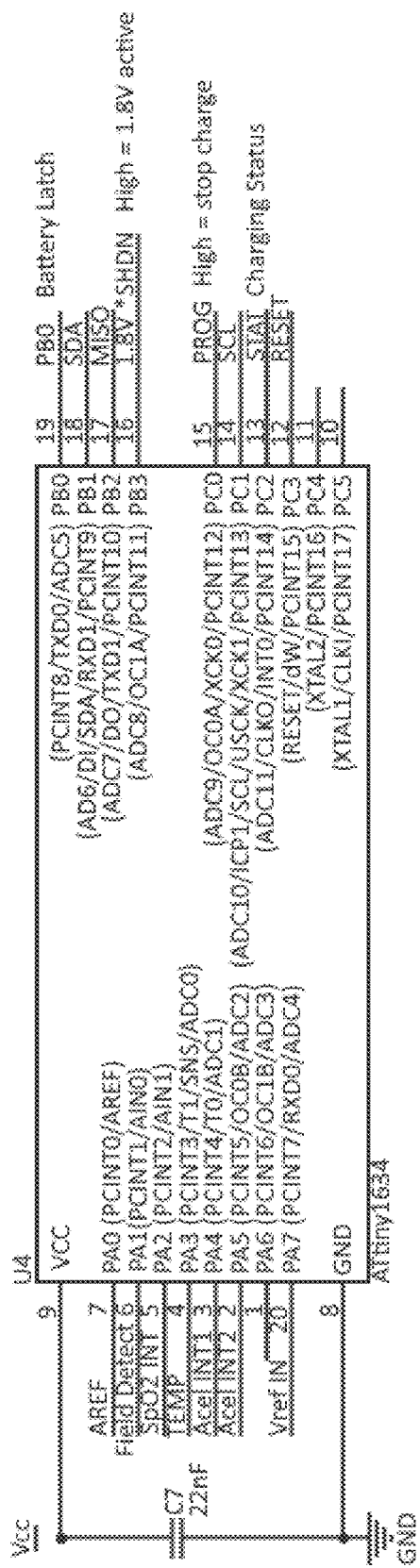
FIG. 13A illustrates one embodiment of a microcontroller.

FIGS. 13A-13G illustrate electronic components of one embodiment of the device. FIG. 13A illustrates one embodiment of a microcontroller. The microcontroller preferably includes at least one memory. In one embodiment, the at least one memory is RAM, ROM, EPROM, EEPROM, and/or FLASH memory. In the embodiment shown in FIG. 13A, the microcontroller is part number ATtiny1634 by Atmel. Information for part number ATtiny1634 is in the datasheet for ATtiny1634, DOC ID Atmel-8303H-AVR-ATtiny1634-Datasheet by Atmel dated February 2014, which is incorporated herein by reference in its entirety. Alternative microcontrollers are compatible with the present invention.

Figure 13B:
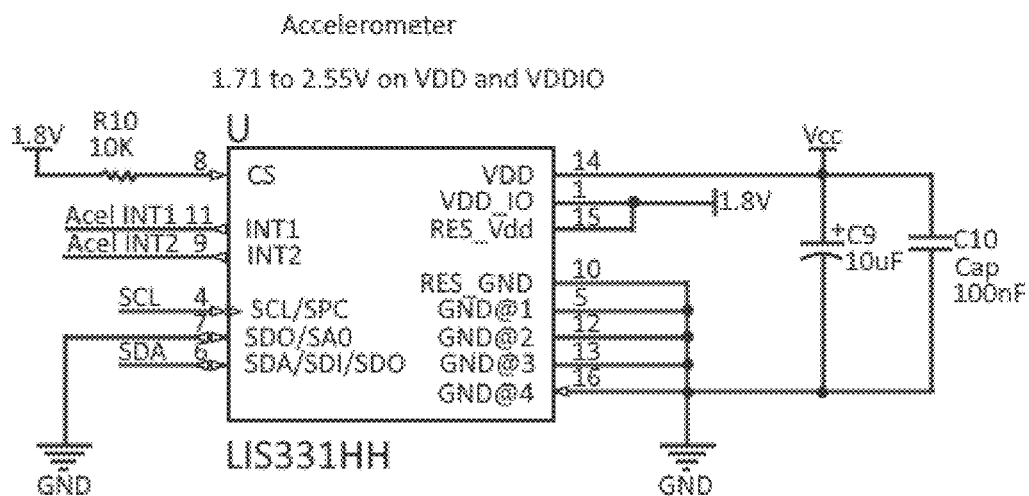
FIG. 13B illustrates one embodiment of an accelerometer.

FIG. 13B illustrates one embodiment of an accelerometer. The accelerometer is preferably a 3-axis accelerometer. The accelerometer is preferably operable to function as a pedometer. In one embodiment, the accelerometer is a MEMS digital output motion sensor. In the embodiment shown in FIG. 13B, the accelerometer is a MEMS digital output motion sensor, part number LIS331HH by STMicroelectronics. Information for part number LIS331HH is in the datasheet for LIS331HH, DOC ID 163366, REV. 1 by STMicroelectronics dated October 2009, which is incorporated herein by reference in its entirety. Alternative accelerometers are compatible with the present invention.

Figure 13C:
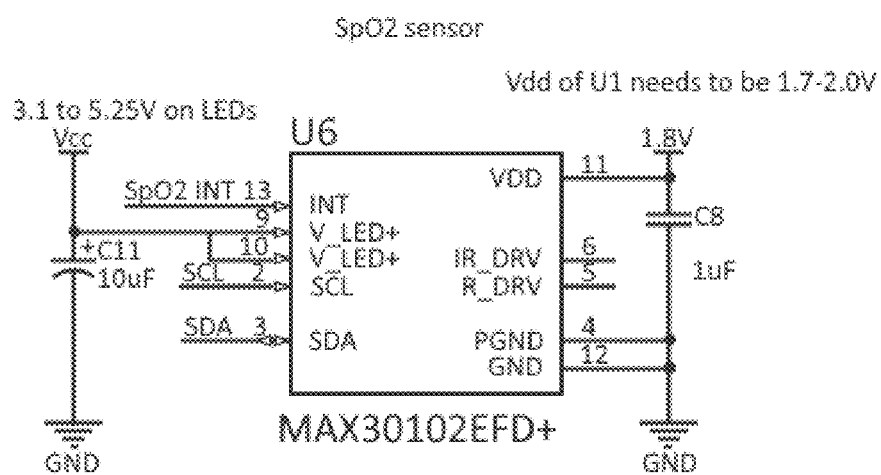
FIG. 13C illustrates one embodiment of an integrated blood oxygen sensor and heart rate monitor.

FIG. 13C illustrates one embodiment of an integrated blood oxygen sensor and heart rate monitor. The blood oxygen sensor is preferably a pulse oximeter. In the embodiment shown in FIG. 13C, the integrated blood oxygen sensor and heart rate monitor is part number MAX30102EFD+ by Maxim Integrated. Information for part number MAX30102EFD+ is in the datasheet for MAX30102, DOC ID 19-7740, REV. 0 by Maxim Integrated dated September 2015, which is incorporated herein by reference in its entirety. Alternative blood oxygen sensors and/or heart rate monitors are compatible with the present invention.

Figure 13D:
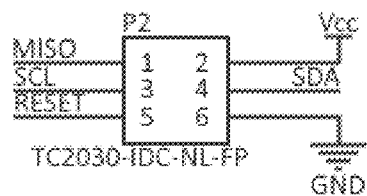
FIG. 13D illustrates one embodiment of a connector that connects debuggers, programmers, and test equipment to a PCB.

FIG. 13D illustrates one embodiment of a connector that connects debuggers, programmers, and test equipment to a printed circuit board (PCB). In the embodiment shown in FIG. 13D, the connector is a Tag-Connect programming pad, part number TC2030-IDC-NL. Alternative connectors are compatible with the present invention.

Figure 13E:
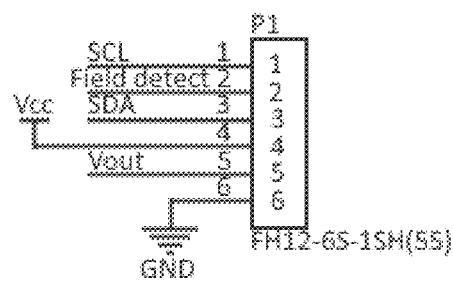
FIG. 13E illustrates one embodiment of an NFC antenna connector.

FIG. 13E illustrates one embodiment of an NFC antenna connector. In the embodiment shown in FIG. 13E, the NFC antenna connector is formed of part number FH12-6S-1SH (55) by Hirose Electric Co. Alternative antenna connectors are compatible with the present invention.

Figure 13F:
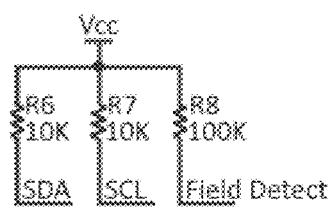
FIG. 13F illustrates one embodiment of pull up resistors connected to the microcontroller in FIG. 13A.

FIG. 13F illustrates one embodiment of pull up resistors connected to the microcontroller in FIG. 13A.

Figure 13G:
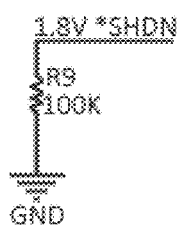
FIG. 13G illustrates one embodiment of a pull down resistor connected to the microcontroller in FIG. 13A.

FIG. 13G illustrates one embodiment of a pull down resistor connected to the microcontroller in FIG. 13A.

Figure 14:
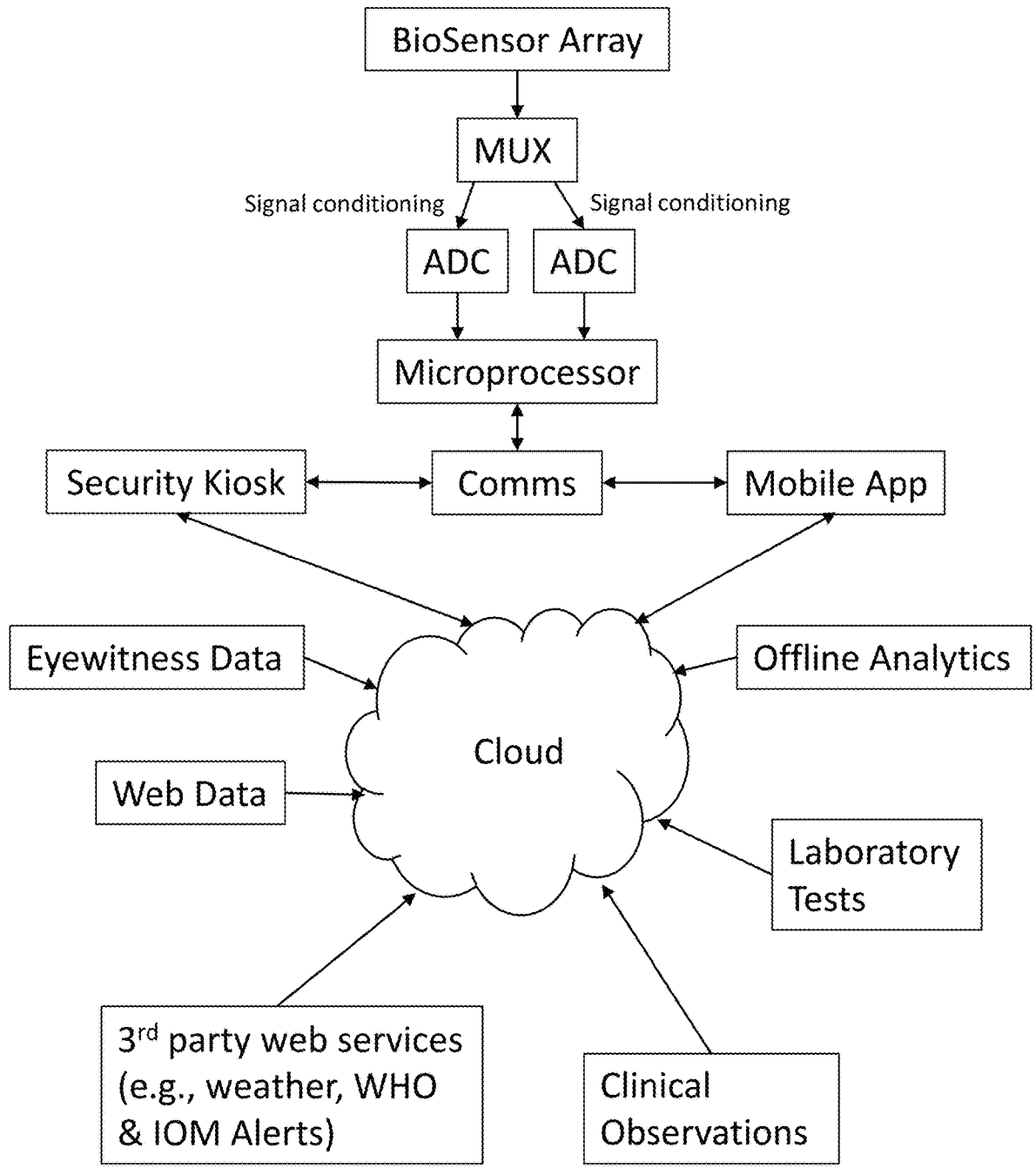
FIG. 14 illustrates a diagram of the system communications.

A diagram of the system communications is shown in FIG. 14. The biosensor array sends signals to a multiplexer (MUX), which pulls in signals from all of the sensors and all of the modalities. The signals are conditioned through a series of capacitors and resistors before the signals are converted using an ADC with a programmable amplifier. The amplifier gain is customized to each sensor signal type. The ADC signals are passed to the microprocessor for processing, converting, and storage. The microprocessor manages read times, gains, processing, and store instructions. Data in storage is extracted via a communications event (e.g., NFC scan, BLUETOOTH read, burst) and transmitted to at least one remote transceiver device (e.g., mobile application on a smartphone or tablet, security kiosk). The remote transceiver device is operable to send the data to a cloud and/or at least one remote computer server for storage and/or processing. Types of output data include but are not limited to concentrations (e.g., molarity, osmolarity, and osmolality), heart rate, oxygen saturation, blood pressure, positive or negative viral and/or bacterial tests, temperatures, glucose levels, pH, accelerometer measurements, SNS measurements, and descriptive statistics (e.g., averages, ratios, trends, and patterns).

The at least one remote transceiver device and the sensor apparatus are operable for two-way cross-communication in real time or near real time. The at least one remote transceiver device is operable to communicate with the sensor apparatus to provide, by way of example and not limitation, commands, electrode calibration, software updates, new or updated algorithms, and/or new or updated modifying variables for algorithms. The sensor apparatus is operable to communicate with the at least one remote transceiver device to provide, by way of example and not limitation, output data, processor health properties (e.g., microcontroller health properties), error codes, electrode maintenance, or malfunction. In a preferred embodiment, the remote transceiver device is operable to allow at least one user to view data from at least one sensor apparatus, including sensor history, output data, and biosignature data for an individual. Additionally, or alternatively, the remote transceiver device is operable to allow at least one user to view data from a plurality of sensor apparatuses, including output data, biosignature data, and overall population trends.

The at least one remote transceiver device and the cloud and/or the at least one remote computer server are operable for two-way cross-communication in real time or near real time. In one embodiment, the cloud and/or the at least one remote computer server is operable to transmit the commands, the electrode calibration, the software updates, the new or updated algorithms, the new or updated modifying variables for algorithms to the at least one remote transceiver device. In another embodiment, the cloud and/or the at least one remote computer server is operable to provide software updates for the at least one remote transceiver device (e.g., updates to the mobile application). The data from the sensor apparatus is augmented by additional information and/or external factors. In one embodiment, the additional information and/or the external factors are stored in the cloud and/or on the at least one remote computer server. For example, the additional information and/or external factors include results of laboratory tests, clinical observations, offline analytics, eyewitness data, web data, and third party web services (e.g., weather, World Health Organization (WHO) and International Organization for Migration (TOM) alerts). Additionally, social media use can be monitored to supplement the data from the sensor apparatus. In a preferred embodiment, the additional information and/or the external factors are processed with the data from the sensor apparatus in the cloud and/or on the at least one remote computer server.

Figure 15:
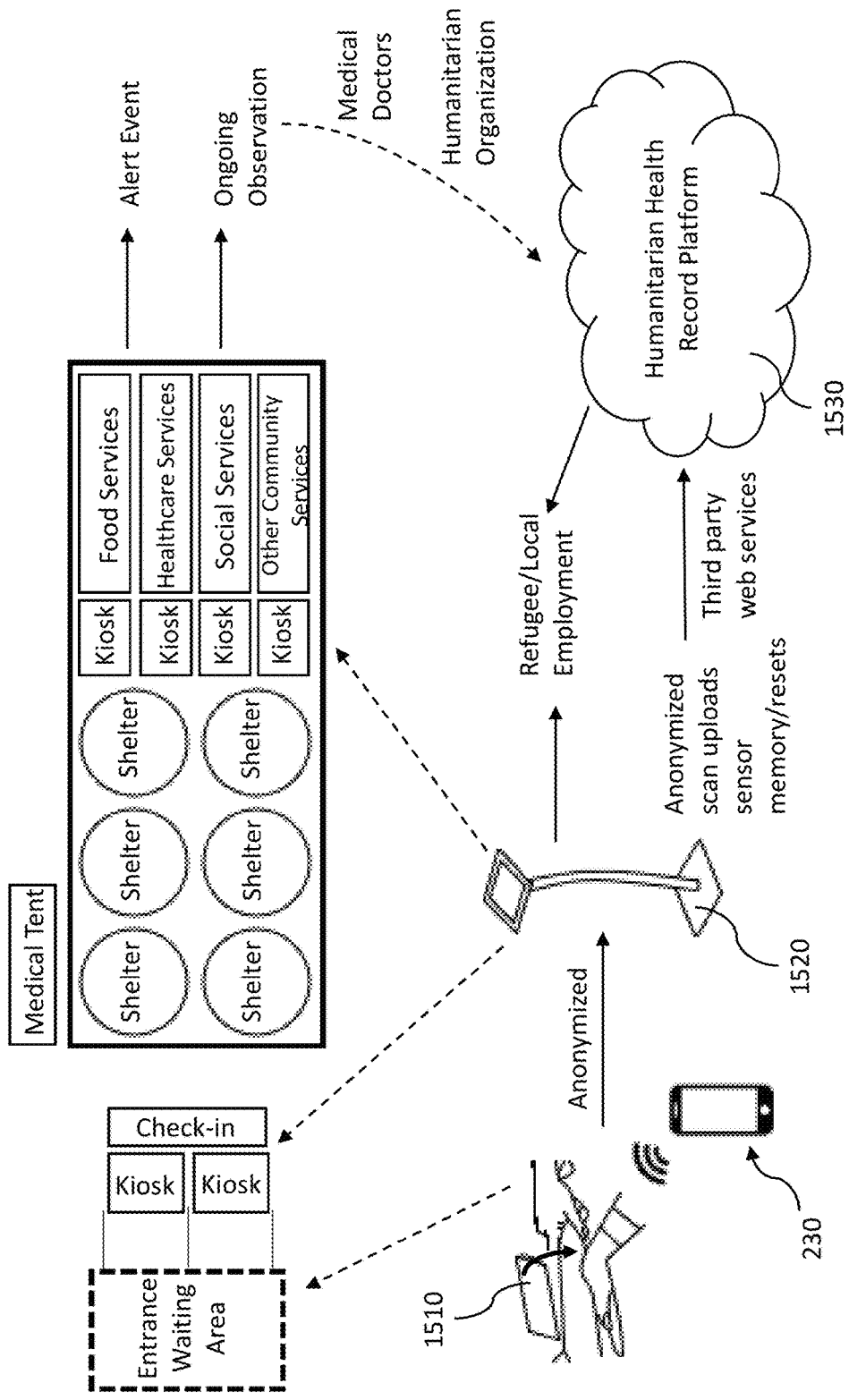
FIG. 15 illustrates one embodiment of the invention as a refugee care system.

FIG. 15 illustrates one embodiment of the invention as a refugee care system. The system is also operable to be used as an air crew safety system, an elderly care system, a crowd care system, an athletic care system, a border or customs risk mitigation system, a disaster triage system, and a military field medical system. As shown in FIG. 15, a device 1510 is placed on a refugee's arm by a humanitarian aid worker. The device 1510 is initialized and begins to collect data. In one embodiment, the device 1510 is initialized by at least one remote transceiver device 230 (e.g., smartphone, tablet). In a preferred embodiment, the data is anonymized. An advanced profile view shows key biomarker trends and discrepancies among the population prior to entry in the refugee camp. The device 1510 is scanned at a bio-scan security kiosk 1520, which uploads the data in the memory of the device 1510 to a humanitarian health record platform 1530 and resets the memory. The humanitarian health record platform 1530 interfaces with third party web services, such as weather, World Health Organization (WHO) alerts, and/or International Organization for Migration (TOM) alerts. The humanitarian health record platform 1530 allows humanitarian organizations (e.g., Red Cross) to observe trends of the population and manage localized disease outbreaks. Additionally, medical doctors are able to provide anonymized individual refugee assistance. In another embodiment, refugees and/or locals are employed to scan the device 1510. In a preferred embodiment, the device 1510 measures a change in heart rate, a change in oxygen saturation, a change in skin temperature, and a change in glucose in 10 second reads every 10 minutes.

Figure 16:
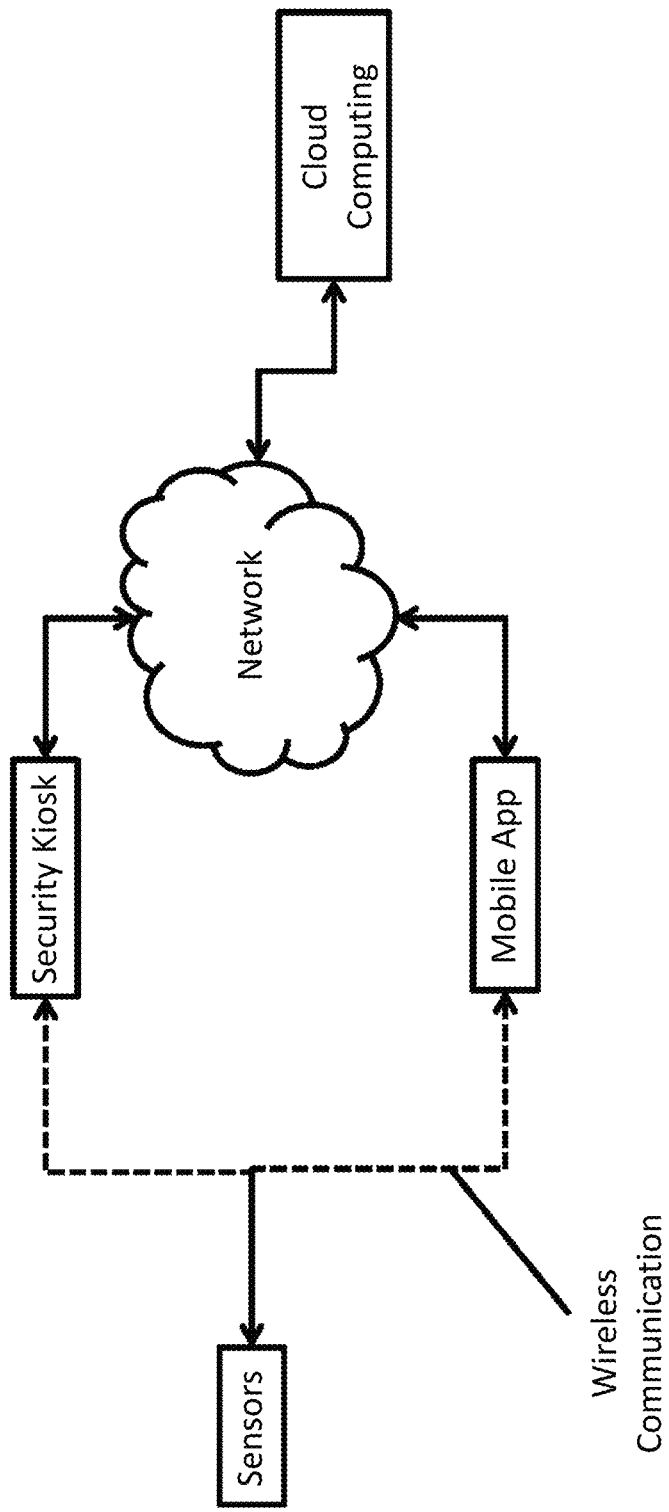
FIG. 16 shows a diagram of the system architecture.
Figure 17:
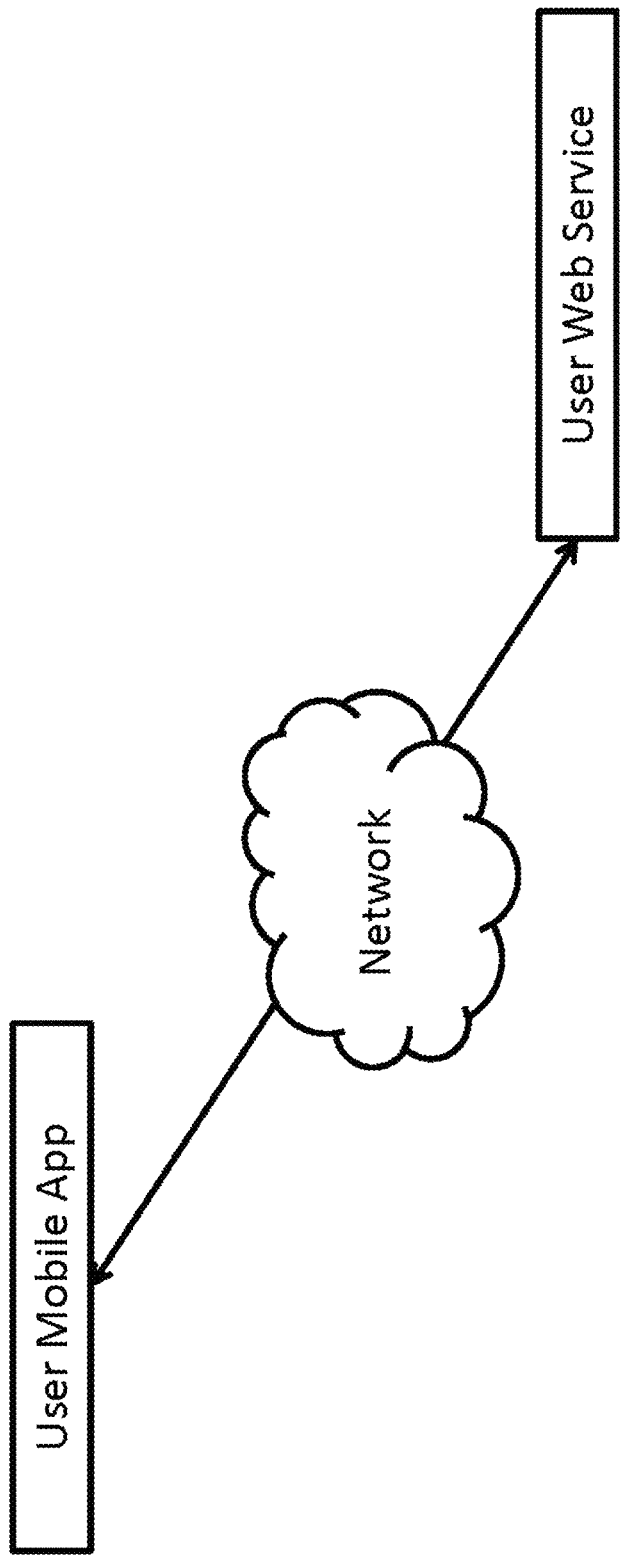
FIG. 17 shows a diagram of the network connection between the user mobile app and the user web service.

A diagram of the system architecture is shown in FIG. 16. The sensor apparatus is in wireless communication with at least one remote transceiver device (e.g., a mobile application, security kiosk). In a preferred embodiment, the mobile application is on a smartphone. Alternatively, the mobile application is on a tablet, a laptop computer, or a desktop computer. In one embodiment, the mobile application is in network communication with a user web service, as shown in FIG. 17, to access the cloud database and a library. In one embodiment, the library includes functions, such as file storage, security, extensions, utilities, scheduling, messaging, persistence, cache, and/or logging.

Figure 18:
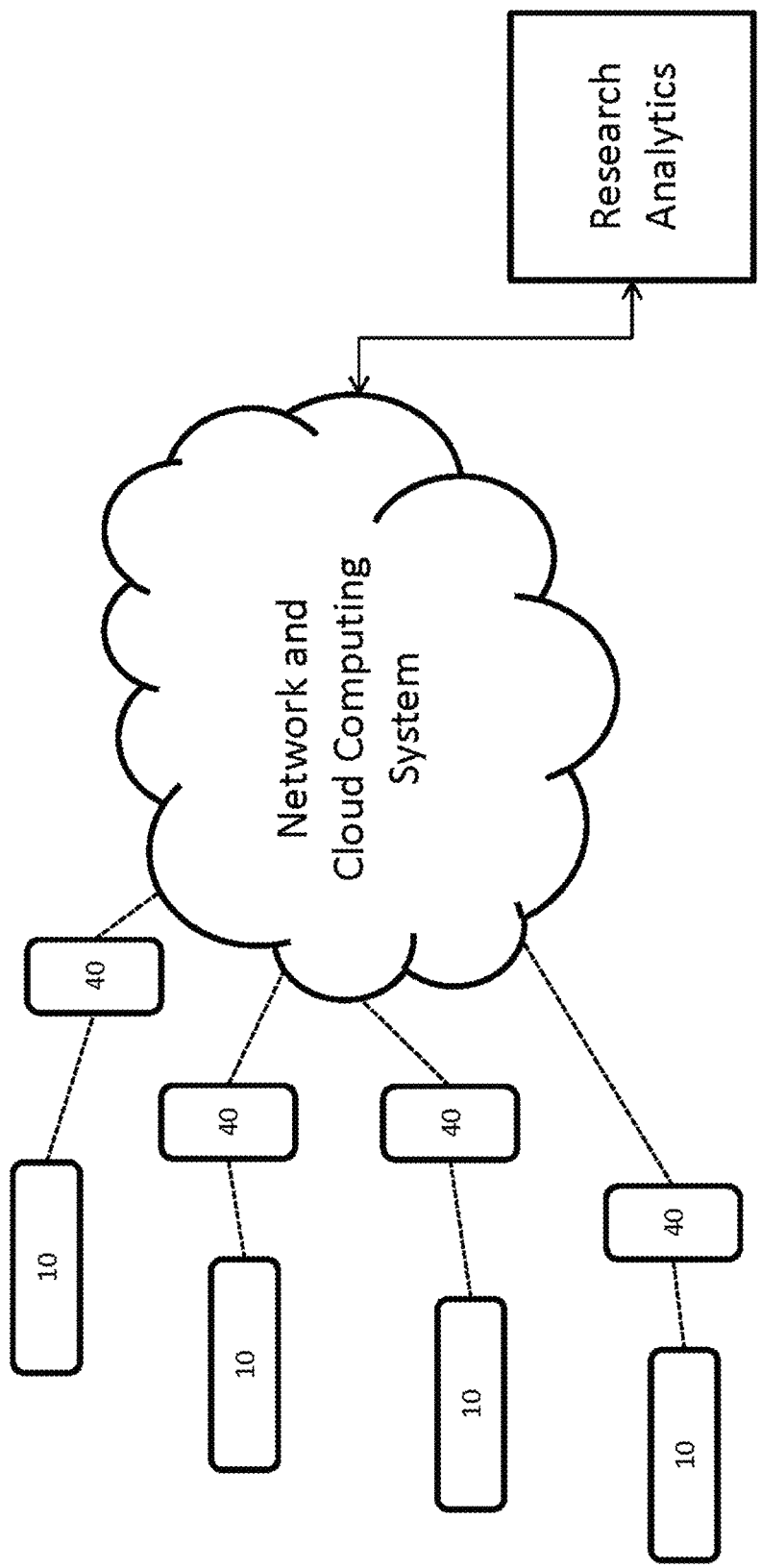
FIG. 18 shows a diagram of a system for public health monitoring and research analytics.

From the cloud computing system, data including X-Mod results from multiple users may be stored, as diagrammed in FIG. 18. Data from a plurality of sensor apparatuses 10 is transmitted to a plurality of remote transceiver devices 40. Data is then transmitted from the plurality of remote transceiver devices 40 to the network and cloud computing system. Data from the network and cloud computing system can be used by researchers, coaches, and public health officials in real time or over time drawing on historical data for research analytics. In a preferred embodiment, the data is from sensor apparatuses with the same configuration, providing greater reliability to the pool of data. The ability to collect biosignature data from a large population of subjects provides a real-time public health research system and method.

Additionally, the ability to collect biosignature data from a large population of subjects provides physicians with a method of monitoring a specific population and/or performing triage. For example, the sensor apparatus can be placed on victims of a disaster, allowing physicians to monitor victims and attend to the most critically injured victims first. The sensor apparatus can also be used to monitor prisoners for health issues and/or fighting. Alternatively, the sensor apparatus can be used to monitor alcoholics or drug addicts for relapse.

Figure 19:
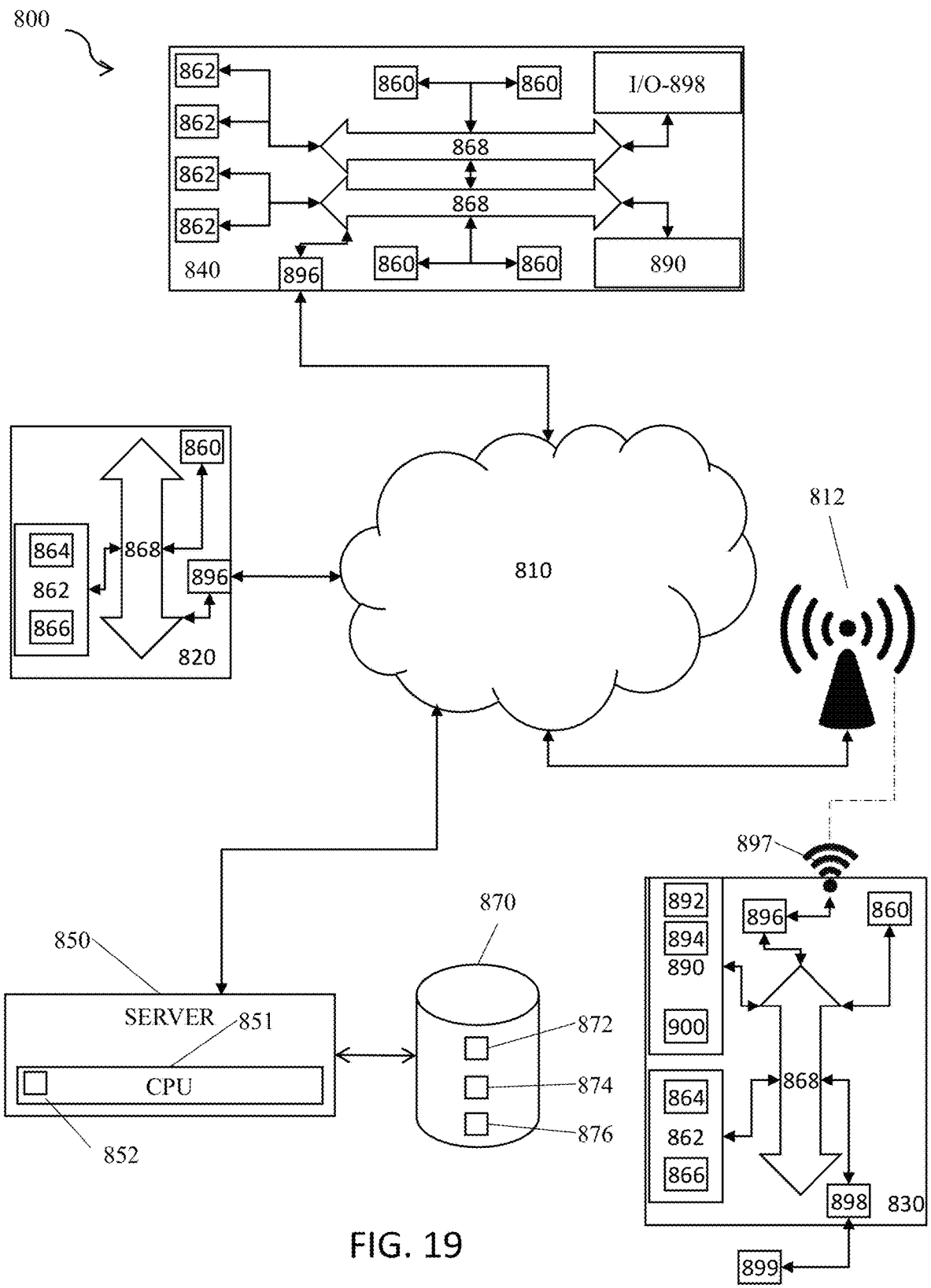
FIG. 19 illustrates a schematic diagram illustrating general components of a cloud-based computer system.

FIG. 19 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 19, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 19, may include other components that are not explicitly shown in FIG. 19, or may utilize an architecture completely different than that shown in FIG. 19. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the glucose sensor can measure glucose levels in blood, interstitial fluid, or sweat using a disposable patch. Sweat sensors can analyze various biomarkers, including glucose, calcium, ammonium, amino acids, hormones, steroids, proteins, and interleukins. The above-mentioned examples are just some of the many configurations that the mentioned components can take on. All modifications and improvements have been deleted herein for the sake of conciseness and readability but are properly within the scope of the present invention.

The invention claimed is:

1. A system for using integrated sensor arrays to measure and analyze multiple biosignatures from a human or an animal comprising:
   an apparatus for sensing and analyzing at least two biosignatures, wherein the apparatus includes a biosensor array, an electronic core, and at least one antenna;
   at least one remote transceiver device; and
   at least one remote computer server;
   wherein the biosensor array comprises at least two sensors, wherein two or more of the at least two sensors are of differing modalities; wherein the differing modalities include imaging, photon, spectroscopy, electrochemical, inertial, thermal, radiofrequency, electromagnetic, and/or ultrasound;
   wherein one or more of the at least two sensors includes at least one sympathetic nervous system (SNS) sensor and at least one non-sympathetic nervous system (non-SNS) sensor;
   wherein the at least one SNS sensor is used to calibrate one or more of the at least one non-SNS sensor;
   wherein the electronic core comprises a multiplexer, at least one analog-to-digital converter, and at least one processor;
   wherein the apparatus analyzes at least two biosignatures from the at least two sensors, calculates at least one output datum of the at least two biosignatures, and transmits the at least one output datum to the at least one remote transceiver device;
   wherein the at least one remote transceiver device transmits the at least one output datum to the at least one remote computer server or at least one remote computing device or database for storage;
   wherein the apparatus and the at least one remote transceiver device have real-time or near-real-time two-way communication;
   wherein the at least one remote transceiver device and the at least one remote computer server have real-time or near-real-time communication; and
   wherein the at least one remote computer server is operable to analyze apparatus data.

2. The system of claim 1, wherein the at least two sensors include a heart rate sensor, a blood oxygen sensor, a blood pressure sensor, a stabilized antibodies sensor, a viral sensor, a bacterial sensor, a temperature sensor, a sweat sensor, a pH sensor, a glucose sensor, an analyte sensor, an electromagnetic sensor, and/or a motion sensor.

3. The system of claim 1, wherein the at least one output datum includes but is not limited to heart rate, oxygen saturation, blood pressure, positive or negative viral and/or bacterial tests, temperatures, glucose levels, pH, accelerometer measurements, SNS measurements, concentrations, such as molarity, osmolarity, and osmolality, and/or descriptive statistics, such as averages, ratios, trends, and patterns.

4. The system of claim 1, wherein the two-way communication further comprises commands, electrode calibration, software updates, new or updated algorithms, new or updated modifying variables for algorithms, processor health properties, error codes, and/or electrode maintenance or malfunction.

5. The system of claim 1, further comprising at least one external factor stored on the at least one remote server device, wherein the at least one external factor is at least one clinical observation, eyewitness data, offline analytics, at least one laboratory test result, weather data, social media analytics, third party data, external research, and/or web data.

6. The system of claim 1, wherein the at least one remote computer server is operable to analyze the apparatus data using cross-modal analytics, wherein the cross-modal analytics include change detection, rates, vectors, cross queues, tips, condition settings, user settings, self-calibrations, personalization, trends, patterns, validations, and/or alerts.

7. The system of claim 1, wherein the at least one remote computer server is operable to generate a personal profile for the human or the animal, wherein the at least one remote computer server is operable to compare apparatus data to the personal profile for the human or the animal and/or at least one situation profile, and wherein the at least one remote computer server is operable to generate at least one alert when the apparatus data deviates from the personal profile for the human or the animal and/or the at least one situation profile.

8. The system of claim 1, wherein the at least one output datum is transmitted from the apparatus to the at least one remote transceiver device through wireless network communication by one or more of the at least one antenna of the apparatus.

9. The system of claim 1, wherein the at least one SNS sensor is configured to measure at least one stress level, wherein the at least one SNS sensor is configured to detect changes in the at least one measured stress level, wherein the at least one SNS sensor is configured to receive a designated stress level range, and wherein the at least one SNS sensor is configured to generate an alert when the at least one measured stress level exceeds the designated stress level range.

10. The system of claim 1, wherein the at least one remote computer server is configured for signal characterization, wherein the signal characterization includes signal gain rate, signal amplitude shape, signal decline, and/or signal phase shifts, and wherein the at least one remote computer server is further configured to use signal characterization to distinguish between cardio stress, pulmonary blood oxygen stress, physical stress, gastro stress, thermoregulation stress, glucose stress, arterial stress, and/or acid stress.

11. The system of claim 1, wherein one or more of the at least two sensors include at least one ion-selective electrode, wherein the ion-selective electrode generates a signal, and wherein the SNS sensor is configured to calibrate the ion-selective electrode signal.

12. The system of claim 1, wherein the apparatus includes a flexible sensor flap, wherein the flexible sensor flap is connected to the electronic core, wherein the sensor flap includes at least one sensor, and wherein the flexible sensor flap is configured to receive at least one sensor upgrade.

13. The system of claim 12, wherein one or more of the at least two sensors include an antibodies sensor, wherein the at least one sensor upgrade includes at least one antigen, wherein the antibodies sensor is configured to detect the presence of the at least one antigen.

14. The system of claim 1, wherein the remote transceiver device includes a software platform, wherein the software platform is configured to identify biomarker trends and discrepancies, and wherein the software platform is configured to identify a disease outbreak.

15. The system of claim 1, wherein the remote transceiver device includes a mobile application, wherein the mobile application includes at least one scheduled advisory action, wherein the at least one scheduled advisory action includes a dietary action, an exercise action and/or a medication action, wherein the scheduled medical advisory action includes a name of a prescription, a dosage of the prescription, a prescription number, a production identification and/ or a picture reminder, wherein the mobile application is configured to determine at least one potential side effect of the prescription, and wherein the mobile application is configured to generate an alert based on the at least one potential side effect.

16. A system for using integrated sensor arrays to measure and analyze multiple biosignatures from a human or an animal comprising:
   an apparatus for sensing and analyzing at least two biosignatures, wherein the apparatus includes a biosensor array, an electronic core, and at least one antenna;
   at least one remote transceiver device; and
   at least one remote computer server;
   wherein the biosensor array comprises at least two sensors, wherein two or more of the at least two sensors are of differing modalities; wherein the differing modalities include imaging, photon, spectroscopy, electrochemical, inertial, thermal, radiofrequency, electromagnetic, and/or ultrasound;
   wherein one or more of the at least two sensors includes at least one sympathetic nervous system (SNS) sensor and at least one non-sympathetic nervous system (non-SNS) sensor;
   wherein the at least one SNS sensor is used to calibrate one or more of the at least one non-SNS sensor;
   wherein the electronic core comprises a multiplexer, at least one analog-to-digital converter, and at least one processor;
   wherein the apparatus analyzes at least two biosignatures from the at least two sensors, calculates at least one output datum of the at least two biosignatures, and transmits the at least one output datum to the at least one remote transceiver device;
   wherein the at least one remote transceiver device transmits the at least one output datum to the at least one remote computer server or at least one remote computing device or database for storage;
   wherein the apparatus and the at least one remote transceiver device have real-time or near-real-time two-way communication;
   wherein the at least one remote transceiver device and the at least one remote computer server have real-time or near-real-time communication;
   wherein at least one external factor is stored on the at least one remote computer server;
   wherein the at least one remote computer server is operable to analyze apparatus data;
   wherein the at least one remote computer server is operable to detect at least one biosignature change and at least one rate of change of the at least one biosignature change;
   wherein the at least one remote computer server is configured to receive at least one designated threshold for at least one biosignature; and
   wherein the at least one remote computer server is operable to generate at least one alert when the at least one biosignature change and the at least one rate of change of the at least one biosignature is greater than the designated threshold.

17. A method for using integrated sensor arrays to measure and analyze multiple biosignatures from a human or an animal, the method comprising:
   providing an apparatus for sensing and analyzing at least two biosignatures, wherein the apparatus includes at least two sensors, at least one analog-to-digital converter, a multiplexer, a processor, and at least one antenna; at least one remote transceiver device; and at least one remote computer server; wherein the at least two sensors includes at least one sympathetic nervous system (SNS) sensor and at least one non-sympathetic nervous system (non-SNS) sensor, wherein the sympathetic nervous system sensor is used to calibrate at least one non-SNS sensor;

wherein the at least one remote transceiver device and the apparatus are operable for two-way cross-communication in real time or near-real time;

each of the at least two sensors sensing at least one biosignature of the human or the animal;

the processor converting the at least one biosignature of the human or the animal into at least one output datum using at least one algorithm;

one or more of the at least one antenna transmitting the at least one output datum to the at least one remote transceiver device via the two-way communication with the apparatus;

the at least one remote transceiver device sharing or transmitting the at least one datum with the at least one remote computer server or at least one remote computing device or database for storage; and the at least one remote computer server analyzing apparatus data.

18. The method of claim 17, wherein the at least one output datum includes but is not limited to concentrations, such as molarity, osmolarity, and osmolality, and/or descriptive statistics, such as averages, ratios, and trends.

19. The method of claim 17, wherein the at least one output datum is transmitted from the apparatus to the at least one remote transceiver device through wireless network communication by one or more of the at least one antenna of the apparatus.

20. The method of claim 17, wherein the at least one remote computer server is operable to analyze the apparatus data using cross-modal analytics, wherein the cross-modal analytics include change detection, rates, vectors, cross queues, tips, condition settings, user settings, self-calibrations, personalization, trends, patterns, validations, and/or alerts.

* * * * *